US009969981B2

(12) United States Patent
Karanu et al.

(10) Patent No.: US 9,969,981 B2
(45) Date of Patent: May 15, 2018

(54) METHODS FOR PURIFYING CELLS DERIVED FROM PLURIPOTENT STEM CELLS

(75) Inventors: Francis Karanu, Skillman, NJ (US); Alireza Rezania, Skillman, NJ (US)

(73) Assignee: Janssen Biotech, Inc., Horsham, PA (US)

(*) Notice: Subject to any disclaimer, the term of this patent is extended or adjusted under 35 U.S.C. 154(b) by 0 days. days.

(21) Appl. No.: 13/036,476

(22) Filed: Feb. 28, 2011

(65) Prior Publication Data

US 2011/0212067 A1 Sep. 1, 2011

Related U.S. Application Data

(60) Provisional application No. 61/309,193, filed on Mar. 1, 2010.

(51) Int. Cl.
*C12N 5/071* (2010.01)
*A61K 35/39* (2015.01)

(52) U.S. Cl.
CPC ............ *C12N 5/0676* (2013.01); *A61K 35/39* (2013.01); *C12N 2500/90* (2013.01); *C12N 2501/115* (2013.01); *C12N 2501/117* (2013.01); *C12N 2501/155* (2013.01); *C12N 2501/16* (2013.01); *C12N 2501/385* (2013.01); *C12N 2501/415* (2013.01); *C12N 2506/02* (2013.01)

(58) Field of Classification Search
CPC .................................................... C12N 5/0676
See application file for complete search history.

(56) References Cited

U.S. PATENT DOCUMENTS

| | | | |
|---|---|---|---|
| 3,209,652 A | 10/1965 | Burgsmueller | |
| 3,845,641 A | 11/1974 | Waller | |
| 3,935,067 A | 1/1976 | Thayer | |
| 4,499,802 A | 2/1985 | Simpson | |
| 4,537,773 A | 8/1985 | Shenvi | |
| 4,557,264 A | 12/1985 | Hinsch | |
| 4,737,578 A | 4/1988 | Evans et al. | |
| 5,215,893 A | 6/1993 | Mason et al. | |
| 5,449,383 A | 9/1995 | Chatelier et al. | |
| 5,525,488 A | 6/1996 | Mason et al. | |
| 5,567,612 A | 10/1996 | Vacanti et al. | |
| 5,665,568 A | 9/1997 | Mason et al. | |
| 5,686,090 A | 11/1997 | Schilder et al. | |
| 5,713,957 A | 2/1998 | Steele et al. | |
| 5,716,810 A | 2/1998 | Mason et al. | |
| 5,718,922 A | 2/1998 | Herrero-Vanrell | |
| 5,759,830 A | 6/1998 | Vacanti et al. | |
| 5,770,417 A | 6/1998 | Vacanti et al. | |
| 5,780,454 A | 7/1998 | Adams et al. | |
| 5,834,308 A | 11/1998 | Peck et al. | |
| 5,843,780 A | 12/1998 | Thomson | |
| 5,888,816 A | 3/1999 | Coon et al. | |
| 5,908,782 A | 6/1999 | Marshank et al. | |
| 5,914,262 A | 6/1999 | MacMichael et al. | |
| 5,942,435 A * | 8/1999 | Wheeler ....................... 435/325 |
| 6,001,647 A | 12/1999 | Peck et al. | |
| 6,022,743 A | 2/2000 | Naughton et al. | |
| 6,087,113 A | 6/2000 | Caplan et al. | |
| 6,083,903 A | 7/2000 | Adams et al. | |
| 6,200,806 B1 | 3/2001 | Thomson | |
| 6,261,549 B1 | 6/2001 | Fernandez et al. | |
| 6,281,012 B1 | 8/2001 | McIntosh et al. | |
| 6,297,217 B1 | 10/2001 | Adams et al. | |
| 6,306,424 B1 | 10/2001 | Vyakarnan et al. | |
| 6,328,960 B1 | 12/2001 | McIntosh et al. | |
| 6,331,298 B1 | 12/2001 | Ferguson et al. | |
| 6,333,029 B1 | 12/2001 | Vyakarnam et al. | |
| 6,365,149 B2 | 2/2002 | Vyakarnam et al. | |
| 6,413,773 B1 | 7/2002 | Ptasznik et al. | |
| 6,436,704 B1 | 8/2002 | Roberts et al. | |
| 6,458,589 B1 | 10/2002 | Rambhatla | |
| 6,458,593 B1 | 10/2002 | Musick et al. | |
| 6,509,369 B2 | 1/2003 | Scott et al. | |
| 6,521,427 B1 | 2/2003 | Evans | |
| 6,534,084 B1 | 3/2003 | Vyakarnam et al. | |

(Continued)

FOREIGN PATENT DOCUMENTS

CN 1389565 A 7/2002
CN 1602351 A 3/2005
(Continued)

OTHER PUBLICATIONS

Inami et al., 2010, Immunology and Cell Biology, pp. 1-8.*
McLean et al., 2007, Stem Cells, vol. 25, pp. 29-38.*
Brevini et al., 2010, Theriogenology, vol. 74, pp. 544-550.*
Paris et al., 2010, Theriogenology, vol. 74, pp. 516-524.*
Munoz et al., 2008, Theriogenology, vol. 69, pp. 1159-1164.*
Narang et al., 2006, Pharmacological Reviews, vol. 58(2), pp. 194-243.*
Ekser et al., Oct. 21, 2011, The Lancet, pp. 1-12.*
Lin et al., 2009, Transplant Immunology, vol. 21, pp. 75-80.*
D'Amour et al., 2006, Nat. Biotechnology, vol. 24(11), pp. 1392-1401.*
Hiemisch et al., 1997, The EMBO J., vol. 16(13), pp. 3995-4006.*
Zulewski et al., 2001, Diabetes, vol. 50, pp. 521-533.*

(Continued)

*Primary Examiner* — Thaian N Ton
*Assistant Examiner* — David A. Montanari
(74) *Attorney, Agent, or Firm* — Lois A. Gianneschi

(57) ABSTRACT

The present invention is directed to methods to differentiate pluripotent stem cells. In particular, the present invention provides methods of characterization of cells differentiated into cells expressing markers characteristic of the pancreatic endocrine lineage utilizing unique surface markers. The present invention also provides methods to enrich or sort cells expressing markers characteristic of the pancreatic endocrine lineage. The present invention also provides methods to deplete cells that may contaminate populations of cells expressing markers characteristic of the pancreatic endocrine lineage formed by the methods of the present invention, thereby reducing the incidence of tumor formation in vivo following transplantation.

12 Claims, 21 Drawing Sheets

(56) References Cited

U.S. PATENT DOCUMENTS

| | | |
|---|---|---|
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 * | 5/2008 | Tsang et al. ............ 435/378 |
| 7,410,773 B2 * | 8/2008 | Abuljadayel ............ 435/7.8 |
| 7,410,798 B2 | 8/2008 | Mandalam et al. |
| 7,413,734 B2 | 8/2008 | Misty et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 * | 3/2009 | D'Amour et al. ......... 435/366 |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,045,736 B2 | 6/2015 | Kelly et al. |
| 2002/0072117 A1 | 7/2002 | Xu |
| 2003/0082155 A1 | 5/2003 | Habener |
| 2003/0138948 A1 | 7/2003 | Fisk et al. |
| 2003/0180268 A1 | 9/2003 | Atala |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis et al. |
| 2011/0229441 A1 | 9/2011 | Benchoua et al. |
| 2011/0280842 A1 | 11/2011 | Melton et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |
| 2014/0186953 A1 | 7/2014 | Rezania |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 92302 B1 | 11/2006 |
| EP | 1873237 A1 | 1/2008 |
| EP | 1391505 B1 | 1/2009 |
| EP | 2088190 A1 | 8/2009 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359030 C1 | 6/2009 |
| RU | 2359671 C2 | 6/2009 |
| WO | 199219759 A2 | 2/1992 |
| WO | 1996040172 A1 | 12/1996 |

(56) References Cited

FOREIGN PATENT DOCUMENTS

| | | |
|---|---|---|
| WO | 199847892 A1 | 10/1998 |
| WO | 199920741 A1 | 4/1999 |
| WO | 200029549 A1 | 5/2000 |
| WO | 200123528 A1 | 4/2001 |
| WO | 200151616 A2 | 7/2001 |
| WO | 200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |
| WO | 2003029445 A1 | 4/2003 |
| WO | 2003042405 A2 | 5/2003 |
| WO | 200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | 2003102134 A2 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004067001 A1 | 8/2004 |
| WO | 2004073633 A1 | 9/2004 |
| WO | 2004087885 A2 | 10/2004 |
| WO | 2004090110 A2 | 10/2004 |
| WO | 2005001077 A2 | 1/2005 |
| WO | 2005080598 A1 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | 2005116073 A3 | 12/2005 |
| WO | 2006016999 A1 | 2/2006 |
| WO | 2006020919 A2 | 2/2006 |
| WO | 2006088867 A2 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006094286 A2 | 9/2006 |
| WO | 2006100490 A1 | 9/2006 |
| WO | 2006108361 A1 | 10/2006 |
| WO | 2006113470 A2 | 10/2006 |
| WO | 2006114098 A2 | 11/2006 |
| WO | 2006126574 A1 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007027157 A1 | 3/2007 |
| WO | 2007030870 A1 | 3/2007 |
| WO | 2007047509 A1 | 4/2007 |
| WO | 2007051038 A2 | 5/2007 |
| WO | 2007069666 A1 | 6/2007 |
| WO | 2007082963 A1 | 7/2007 |
| WO | 2007101130 A2 | 9/2007 |
| WO | 2007103282 A1 | 9/2007 |
| WO | 2007127927 A2 | 11/2007 |
| WO | 2007139929 A2 | 12/2007 |
| WO | 2007143193 A1 | 12/2007 |
| WO | 2007149182 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2009096049 A1 | 5/2008 |
| WO | 2008086005 A1 | 7/2008 |
| WO | 2008094597 A2 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | 2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010051223 A1 | 5/2010 |
| WO | 2010053472 A1 | 5/2010 |
| WO | 2010057039 A2 | 5/2010 |
| WO | 2010059775 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055397 A1 | 4/2013 |
| WO | 2013055834 A2 | 4/2013 |
| WO | 2013095953 A1 | 6/2013 |
| WO | 2013184888 A1 | 12/2013 |
| WO | 2014033322 A1 | 3/2014 |
| WO | 2014105546 A1 | 7/2014 |
| WO | 2014152321 A1 | 9/2014 |

OTHER PUBLICATIONS

Petitte et al., 2004, Mech. of Develop., vol. 121, pp. 1159-1168.*
Lavial et al., 2010, Develop. Growth Diff., vol. 52, pp. 101-114.*
Zhang et al. (1993, Zhi Yan Sheng Wu Xue Bao, vol. 26(1), Abstract Only).*
Itkin-Ansari et al. (2005, Developmental Dynamics, vol. 233, pp. 946-953).*
Read et al. (2009, Cancer Cell, vol. 15, pp. 135-147).*
Wang et al. (2005, Diabetes, vol. 54, pp. 2080-2089).*
Brimble et al. (2007, Stem Cells, vol. 25, pp. 54-62).*
Sugiyama et al. (2006, PNAS, vol. 104(1), pp. 175-180).*
Nakase et al. (1996, Am. J. Clin. Pathol., vol. 105, pp. 761-768).*
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J, Proteasome Inhibition in Cancer: Development of PS-341, Seminars in Oncology, 2001, pp. 613-619, vol. 28, No. 6.
Age-Related Eye Disease Study Research Group, a Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

(56) References Cited

OTHER PUBLICATIONS

Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, the Leucocyte Antigen Facts Book, 1997, Textbook, 2[sup] edition, Academic Press.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, the Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.
Brevini, et al., No Shortcuts to Pig Embryonic Stem Cells, Theriogenology, 2010, pp. 544-550, vol. 74.
Bross, et al., Approval Summary for Bortezomib for Injection in the Treatment of Multiple Myeloma, Clinical Cancer Research, Jun. 15, 2004, pp. 3954-3964, vol. 10.
Brown, et al., Optimal Control of Blood Glucose: The Diabetic Patient or the Machine?, Science Translation Medicine, Apr. 14, 2010, pp. 1-5, vol. 2 Issue 27.
Burkard et al, Conditional Neuronal Nitric Oxide Synthase Overexpression Impairs Myocardial Contractility, Circulation Reseach, Jan. 18, 2007, pp. e32-e44, vol. 100.
Buzzard et al., Karyotype of human ES cells during extended culture, Nature, Apr. 1, 2004, 381-382, 22-4, Nature Publishing Group.
Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.
Castaing, et al., Blood Glucose Normalization Upon Transplantation of Human Embryonic Pancreas into Beta-Cell-Deficient SCID Mice, Diabetologica, 2001, pp. 2066-2076, vol. 44.
Chambers, et al., Functional Expression Cloning of Nanog, a Pluripotency Sustaining Factor in Embryonic Stem Cells, Cell, May 30, 2003, pp. 643-655, vol. 113.
Chapple, et al., Unfolding Retinal Dystrophies: A Role for Molecular Chaperones?, Trends in Molecluar Medicine, 2001, pp. 414-421, vol. 7, No. 9.
Chen, et al., A Small Molecule that Directs Differentiation of Human ESCs into the Pancreatic Lineage, Nature Chemical Biology, Apr. 11, 2009, pp. 258-265, vol. 5, No. 4.
Chen, et al., Chemically Defined Conditions for Human iPSC Derivation and Culture, Nature Methods, 2011, pp. 424-429, vol. 8, Issue 5.
Chen, et al., Differentiation of Rat Marrow Mesencymal Stem Cells in Pancreatic Islet Beta-Cells, World Journal of Gastroenterology, Oct. 15, 2004, pp. 3016-3020.
Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.
Cheon, et al., Defined Feeder-Free Culture System of Human Embryonic Stem Cells, Biol Reprod, 2005, 105.046870, DOI10/1095.
Chung, et al., Human Embryonic Stem Cell Lines Generated without Embryo Destruction, Cell Stem Cell, 2008, pp. 113-117, vol. 2.
Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.
Crane, et al., An Embryogenic Model to Explain Cytogenetic Inconsistencies Observed in Chorionic Villus Versus Fetal Tissue, Prenatal Diagnosis, 1988, pp. 119-129, vol. 8.
Cresta, et al., Phase I Study of Bortezomib with Weekly Paclitaxel in Patients with Advanced Solid Tumours, European Journal of Cancer, 2008, pp. 1829-1834, vol. 44.
Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.
D'Amour et al., Efficient differentiation of human embryonic stem cells to definitive endoderm, Nature Biotechnology, Oct. 28, 2005, 1-8, :W.1038/nbt1163, Nature Publishing Group.
D'Amour et al., Production of pancreatic hormone—expressing endocrine cells from human embryonic stem cells, Nature Biotechnology, Oct. 19, 2006, 1392-1401, 24-11, Nature Publishing Group, US.
David M. Chacko, et al., Survival and Differentiation of Cultured Retinal Progenitors Transplanted in the Subretinal Space of the Rat,

(56) References Cited

OTHER PUBLICATIONS

Biochemical and Biophysical Research Communications, 2000, pp. 842-846, vol. 268, Academic Press.
De Coppi, et al., Isolation of Amniotic Stem Cell Lines with Potential for Therapy, Nature Biotechnology, 2007, pp. 100-106, vol. 25, No. 1.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, the Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, the Endocrine Society.
Hadley, et al., Extracellular Matrix Regulates Sertoli Cell Differentiation, Testicular Cord Formation, and Germ Cell Development In Vitro, the Journal of Cell Biology, Oct. 1985, 1511-1522, 101, Rockefeller University Press.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Hichem Frigui, et al., A Robust Competitive Clustering Algorithm With Applications in Computer Vision, IEEE, May 1, 1999, 450-465, 21-5, IEEE, US.
Ho, et al., Animal Cell Bioreactors, Animal Cell Bioreactors, 1991, 1-512, Hardcover, Butterworth-Heinemann.

(56) References Cited

OTHER PUBLICATIONS

Hoehn, et al., Morphological and Biochemical Heterogeneity of Amniotic Fluid Cells in Culture, Methods in Cell Biology, 1982, pp. 11-34, vol. 26, Academic Press, Inc.

Hoffman, et al., Characterization and Culture of Human Embryonic Stem Cells, Nature Biotechnology, 2005, pp. 699-708, vol. 23, No. 6.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, the Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, the Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Kleinman et al., Basement Membrane Complexes with Biological Activity, Biochemistry, 1986, 312-318, 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Biointerphases, Dec. 2009, pp. 6979.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibitio not the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.

Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a Rock Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, the Company of Biologists.

Lanza, et al., Characteristics and Characterization of Human Pluripotent Stem Cells, Stem Cell Anthology, 2010, pp. 141, 142, 144 and 146, 1st Edition.

Laplante, et al., RhoA/Rock and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Protein Kinase A- and C- Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Levenstein et al., Basic Fibroblast Growth Factor Support of Human Embryonic Stem Cell Self-Renewal, Stem Cells, Nov. 10, 2005, 568-574, 24, AlphaMed Press.

(56) References Cited

OTHER PUBLICATIONS

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.
Lilja et al., Cyclin-dependent Kinase 5 Promotes Insulin Exocytosis, Journal of Biological Chemistry, Jul. 6, 2001, 34199-34205, 36-7, JBC Papers in Press.
Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.
Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.
Loh, et al., Genomic Approaches to Deconstruct Puripotency, Annu Rev Genomics Hum Genet, 2011, pp. 165-185, vol. 12.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, 1389-1394, 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
MacFarlane, et al., Glucose Stimulates Translocation of the Homeodomain Transcription Factor PDX1 from the Cytoplasm to the Nucleus in Pancreatic B-Cells, the Journal of Biological Chemistry, 1999, pp. 1011-1016, vol. 274, No. 2.
Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.
Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al, Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.

Michael J. Borowitz, et al., Prognostic Significance of Fluorescence Intensity of Surface Marker . . . , Blood, Jun. 1, 1997, 3960-3966, 89-11, American Society of Hematology, Washington, D.C., US.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.

(56) References Cited

OTHER PUBLICATIONS

Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Pancreatic Endoerm, http://www.rndsystems.com/molecule_group.aspx?g=801&r, 1 page web printout.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Coming CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, the EMBO Journal, 2007, pp. 4744-4755, vol. 26.
Peter O. Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
R&D Systems, Embryonic & Induced Pluripotent Stem Cell Transcription Factors, http://www.mdsystems.com/molecule_group.aspx?r=1&g-3041, 2 page web printout.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.

Reubinoff et al., Embryonic stem cell lines from human blastocysts: somatic differentiation in vitro, Nature Biotech, Apr. 18, 2000, 399-404, 18, Nature America Inc.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Scullica, et al., Diagnosis and Classification of Macular Degenerations: an Approach Based on Retinal Function Testing, Documenta Ophthalmologica, 2001, pp. 237-250, vol. 102.
Seaberg et al., Clonal identification of multipotent precursors from adult ~ mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, the New England Journal of Medicine, Jul. 27, 2000, pp. 230-238, vol. 343, No. 4, the Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.

(56) References Cited

OTHER PUBLICATIONS

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shim, et al., Directed Differentiation of Human Embryonic Stem Cells Towards a Pancreatic Cell Fate, Diabetologia, 2007, pp. 1228-1238, vol. 50.
Schindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monoclonal Antibody Induces Regression of Human Prostate Cancer Xenografts in Nude Mice, the Prostate, Mar. 2, 2001, 47-53, 48, Wiley-Liss, Inc.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Stadtfeld, et al, Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stephen D. De Rosa, 11-color, 13-parameter flow cytometry: Identification of . . . , Nature, Feb. 1, 2001, 245-248, 7-2, Nature Publishing Group, US.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Takahashi, et al., Homogenous Seeding of Mesenchymal Stem Cells into Nonwoven Fabric for Tissue Engineering, Tissue Engineering, 2003, pp. 931-938, vol. 9, No. 5.
Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Currenl Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos One, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Vacuum Cell Seeding: a New Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.

(56) References Cited

OTHER PUBLICATIONS

Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=lnhibin beta B Chain; AltName: Full=Activin beta-B chain; Flags; Precurso, Database UniF7rot [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, the Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, a Doctoral Thesis of Chinese PLA Acadamey of Military Medical Sciences, 2003, 1-127, 1-127 (with English Abstract).
Zhang, et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, the Amerian Society for Biochemistry and molecular Biology, Inc.
Zhao, et al., Derivation and Characterization of Hepatic Progenitor Cells from Human Embryonic Stem Cells, PLoS One Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.
Rezania, et al., Maturation of Human Embryonic Stem Cell-Derived Pancreatic Progenitors into Functional Islets Capable of Treating Pre-Existing Diabetes in Mice, Diabetes, 2012, pp. 2016-2029, vol. 61.
Abe, et al., Evidence That Pl3K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Ali, et al., Exploitation of Protein Kinase C: A Useful Target for Cancer Therapy, Cancer Treatment Reviews, 2009, 1-8, vol. 35 pp.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Best, et al., Embryonic Stem Cells to Beta-Cells by Understanding Pancreas Development, Molecular and Cellular Endorinology, 2008, pp. 86-94, vol. 288.
Bo, et al., Research Progress of Pancreatic Islet Development and Pancreatic Stem Cells, Journal of Clinical Surgery, 2009, pp. 208-210, vol. 17, No. 3.
Brevini et al, Embryonic Stem Cells in Domestic Animals, Embryonic Stem Cells in Domestic Animals, 2010, pp. 544-550, vol. 74.
Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.
Chetty, et al., A Simple Tool ti Improve Pluripotent Stem Cell Differentiation, Nature Methods, 2013, pp. 553-558, vol. 10, No. 6.

(56) References Cited

OTHER PUBLICATIONS

Choi, et al, In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

D'Amour et al, Production of pancreatic hormone, Nature Biotechnology, 2006, pp. 1392-1401, vol. 24.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Deramaudt, et al., The PDX1 Homeodomain Transcription Factor Negatively Regulates the Pancreatic Ductal Cell-specific Keratin 19 Promoter, Journal of Biological Chemistry, 2006, pp. 38385-38395, vol. 281, No. 50.

Dufour, et al., Development of an Ectopic Site for Islet Transplantation Using Biodegradable Scaffolds, Tissue Engineering, 2005, pp. 1323-1331, vol. 11, No. 9/10.

Florio, et al., Activin A Stimulates Insulin Secretion in Cultured Human Pancreatic Islets, J. Endocrinol. Invest., 2000, pp. 231-234, vol. 23.

Foster, et al., Differentiation of Transplanted Microencapsulated Fetal Pancreatic Cells, Experimental Transplantation, Jun. 15, 2007, pp. 1440-1448, vol. 83, No. 11.

Gibco, Solutions for Life Science Research and Drug Discovery, Catalogue Cell Culture Products, 2004-2005, pp. 1-4E, 281406 26 5 27.

Gittest, Developmental Biology of the Pancreas: A comprehensive Review, Developmental Biology, 2009, pp. 4-35, vol. 326, No. 1.

Gordon Weir, Do stem cells hold the key to creation of a cure for diabetes?, Diabetes Voice, 2008, pp. 29-31, Edition 53, No. 2.

Gregg Duester, Retionoic Acid Synthesis and Signaling During Early Organogenesis, Cell, 2008, pp. 921-931, vol. 134.

Hainsworth, et al., Retinal Capillar Basement Membrane Thickening in a Porcine Model of Diabetes Mellitus, Comp Med, 2002, pp. 523-529, vol. 52.

Hay, et al., Highly Efliicient Differentiation of hESCs to Functional Hepatic Endoderm Requires ActivinA and Wnt3a Signaling, PNAS, 2008, pp. 12301-12306, vol. 105, No. 34.

Heinis, et al., HIF1a and Pancreatic Beta-Cell Development, the FASEB Journal, 2012, pp. 2734-2742, vol. 26.

Heinis, et al., Oxygen Tension Regulates Pancreatic Beta-Cell Differentiation Through Hypoxia-Inducible Factor 1x, Diabetes, 2010, pp. 662-669, vol. 59.

Heit, et al., Embryonic Stem Cells and Islet Replacement in Diabetes Mellitus, Pediatric Diabetes, 2004, pp. 5-15, vol. 5.

Heremans, et al., Recapitulation of Embryonic Neuroendocrine Differentiation in Adult Human Pancreatic Duct Cells Expressing Neurogenin 3, the Journal of Cell Biology, 2002, pp. 303-311, vol. 159.

Herrera, Adult-Insulin-and Glucagon-Producing Cells Differentiate from Two Independent Cell Lineages, Development, 2000, pp. 2317-2322, vol. 127, No. 11.

Hosoya, et al., Induction of Differentiation of Undifferentiated Cells into Pancreatic Beta-Cells in Vertebrates, Int. J. Dev. Biol., 2012, pp. 313-323, vol. 56.

Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.

Karvonen, et al., Incidene of Childhood Type 1 Diabetes Worldwide, Diabetes Care, 2000, pp. 1516-1526, vol. 23, No. 10.

Konstantinova et al., 2007, EphA-Ephrin-A-Mediated Beta Cell Communication Regulates Insulin Secretion from Pancreatic Islets, Cell, Apr. 20, 2007, pp. 359-370, vol. 129.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Larsen, et al., Use of the Gootingen Minipig as a Model of Diabetes, with Special Focus on Type 1 Diabetes Research, ILAR Journal, 2004, pp. 303-313, vol. 45, No. 3.

Lee, et al., PKC-Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Leon-Quinto, et al., In Vitro Directed Differentiation of Mouse Embryonic Stem Cells into Insulin-Producing Cells, Diabetologia, 2004, pp. 1442-1451, vol. 47, No. 8.

Li, et al., Pluripotency Can be Rapidly and Efficiently Induced in Human Amniotic Fluid-Derived Cells, Human Molecular Genetics, 2009, pp. 4340-4349, vol. 18, No. 22.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

Munoz et al, Conventional pluripotency markers, Theriogenology, Feb. 7, 2014, pp. 1159-1164, vol. 69.

Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.

Ouziel-Yahalom, et al., Expansion and Redifferentiation of Adult Human Pancreatic islet Cells, Biochemical and Biophysical Research Communications, 2006, pp. 291-298, vol. 341.

Paris, et al, Embryonic Stem Cells in Domestic Animals, Embryonic Stem Cells in Domestic Animals, Feb. 7, 2014, 516-524, 74.

Perrier, et al., Derivation of Midbrain Dopamine Neurons from Human Embryonic Stem Cells, PNAS, Aug. 24, 2004, pp. 12543-12548, vol. 101, No. 34.

Phillips, et al., Directed Differentiation of Human Embryonic Stem Cells into the Pancreatic Endocrine Lineage, Stem Cells and Development, 2007, pp. 561-578, vol. 16, No. 4.

Ptasznik, et al., Phosphatidylinositol 3-Kinase Is a Negative Regulator of Cellular Differentiation, the Journal of Cell Biology, 1997, pp. 1127-1136, vol. 137, No. 5.

Ramiya, et al., Reversal of Insulin-Dependent Diabetes Using Islets Generated in vitro from Pancreatic Stem Cells, Nature Medicine, 2000, pp. 278-281, vol. 6.

Rezania, e al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.

Ross, et al., Cytochrome P450s in the Regulation of Cellular Retinoic Acid Metabolism, Annu. Rev. Nutr., 2011, pp. 65-87, vol. 31.

Sander, et al., Homeobox Gene Nkk6.1 Lies Downstream of Nkx2.2 in the Major Pathway of Betta-Cell Formation in the Pancreats, Development, 2000, pp. 5533-5540, vol. 127.

Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, vol. 102, No. 20.

Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.

Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.

Soria, et al., From Stem Cells to Beta Cells: New Strategies in Cell Therapy of Diabetes Mellitus, Diabetologia, 2001, pp. 407-415, vol. 44.

Soria, et al., Insulin-Secreting Cells Derived From Embryonic Stem Cells Normalize Glycemia in Streptozotocin-Induced Diabetic Mice, Diabetes, 2000, pp. 157-162, vol. 49, No. 2.

(56) References Cited

OTHER PUBLICATIONS

Spence, et al., Translation Embryology: Using Embryonic Principles to Generate Pancreatic Endocrine Cells from Embryonic Stem Cells, Developmental Dynamics, 2007, pp. 3218-3227, vol. 236.
Stafford, et al., Retinoids Signal Directly to Zebrafish Endoderm to Specify Insuilin-Expressing B-cells, Development, 2005, pp. 949-956, vol. 133.
Stoffel, et al., Navigating the Pathway from Embryonic Stem Cells to Beta Cells, Seminars in Cell & Developmental Biology, 2004, pp. 327-336, vol. 15.
Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.
Suzuken, Differentiation of Multifunctional Stem Cells Using Human Feeder Cells, Research Papers of the Suzuken Memorial Foundation, 2007, pp. 193-197, vol. 24, JP.
Swindle, et al., Swine in Biomedical Research: Management and Models, ILAR News, 1994, pp. 1-5, vol. 36, No. 1.
Totonchi, et al., Feeder-and Serum-Free Establishment and Expansion of Human Induced Pluripotent Stem Cells, Int. J. Dev. Biol., 2010, pp. 8770886, vol. 54.
Tsuchida, et al., Activin Isoforms Signal Through Type I Receptor Serine/Threonin Kinase ALK7, Molecular and Cellular Endocrinology, 2004, pp. 59-65, vol. 22.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.
Jiang, et al., In Vitro Derivation of Functional Insulin-Producing Cells from Human Embryonic Stem Cells, Cell Research, 2007, pp. 333-344, vol. 17.
Rezania, et al., Enrichman of Human Embryonic Stem Cell-Derived NKX6.1—Expressing Pancreatic Progenitor Cells Accelerates the Maturation of Insulin-Secreting Cells In Vivo, Stem Cells, 2013, pp. 2432-2442, vol. 31.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Brimble, S., et al., The Cell Surface Glycosphingolipids SSEA-3 and SSEA-4 Are Not Essential for Human ESC Pluripotency, Stem Cells, Jan. 2007, pp. 54-62, vol. 25.
Buta, et al., Reconsidering pluripotency tests: Do we still need teratoma assays?, Stem Cell Research, Mar. 26, 2013, pp. 552-562, vol. 11.
Chen, et al., Retinoic acid signaling is essential for pancreas development and promotes endocrine at the expense of exocrine cell differentiation in Xenopus, Developmental Biology, May 4, 2004, pp. 144-160, vol. 271.
Cirulli, et al., Netrins: beyond the brain, Molecular Cell Biology, Apr. 2007, pp. 296-308, vol. 8.
Cohick, et al., The Insulin-Like Growth Factors, Annual Reviews Physiol, 1993, pp. 131-153, vol. 55, Annual Reviews Inc.
Furue, et al., Heparin promotes the growth of human embryonic stem cells in a defined serum-free medium, PNAS, Sep. 9, 2008, pp. 13409-13414, vol. 105 Issue 36.
Gibco, Insulin-Transferin-Selenium-X 100X, Invitrogen Cell Culture, Apr. 2005, pp. 1, Form No. 3032.
Gomez, et al., Derivation of cat embryonic stem-like cells from in vitro-produced blastocysts on homologous and heterologous feeder cells, Theriogenology, May 11, 2010, pp. 498-515, vol. 74.
Gordon Weir., Do stem cells hold the key to a future cure for diabetes?, Diabetes Voice, Jun. 2008, pp. 29-31, vol. 53 Issue 2.
Hebrok, et al., Notochord repression of endodermal Sonic hedgehog permits pancreas development, Genes & Development, Apr. 2, 1998, pp. 1705-1713, vol. 12 , Issue 11, Cold Spring Harbor Laboratory Press.
Hiemisch, H., et al., Transcriptional Regulation in Endoderm Development: Characterization of an Enhancer Controlling Hnf3g Expression by Transgenesis and Targeted Mutagenesis, the EMBO Journal, 1997, 3995-4006, vol. 16(13).
Jaenisch, et al., Stem Cells, the Molecular Circuitry of Pluripotency and Nuclear Reprogramming, cell, Feb. 22, 2008, pp. 567-582, vol. 132, Elsevier Inc.
Jean, et al., Pluripotent genes in avian stem cells, Development Growth & Differentitaion, 2013, pp. 41-51, vol. 55.
Kang, et al., Plasma treatment of textiles—Synthetic Polymer-Based Textiles, AATCC Review, 2004, pp. 29-33.
King, et al., Bioreactor development for stem cell expansion and controlled differentiation, Current Opinion in Chemical Biology, Jul. 25, 2007, pp. 394-398, vol. 11, Elsevier Ltd.
Klajnert, et al., Fluorescence studies on PAMAM dendrimers interactions with bovine serum albumin, Bioelectrochemistry, 2002, pp. 33-35, vol. 55.
Kubota,et al., Growth factors essential for self-renewal and expansion of mouse spermatogonial stem cells, cell Biology, Nov. 23, 2004, pp. 16489-16494, vol. 101 , Issue 47.
Kunisada, et al., Small molecules induce efficient differentiation into insulin-producing cells from human induced pluripotent stem cells, Stem Cell Research, Oct. 11, 2011, pp. 274-284, vol. 8.
Lavial, etal., Chicken Embryonic Stem Cells as a Non-Mammalian Ebryonic Stem Cell Model, Development Growth Differentiation, Jan. 2010, pp. 101-114, vol. 52(1).
Lin, C., et al., Coagulation Dysregulatin as a Barrier to Xenotransplantation n the Primate, Transplant Immunology, 2009, pp. 75-80, vol. 21.
McMahon, et al., Noggin-mediated antagonsim of BMP signaling is required for growth and patterning of the neural tube and somite, Genes & Development, Mar. 16, 1998, pp. 1438-1452, vol. 12.
Nakase, et al., Myeliod Antigen, CD13, CD14, and/ or CD33 Expression is Restricted to Certain Lymphiod Neoplasms, Hematopathology, Jun. 1996, pp. 761-768, vol. 105 Issue 6.
Narang, A., et al., Biological and Biomaterial Approaches for Improved Islet Transplantation, Pharmacological Review, Jun. 2006, pp. 194-243, vol. 58(2).
Nostro, et al., Generation of Beta Cells from Human Pluripotent Stem Cells: Potential for Regenerative Medicine, Seminars in Cell & Developmental Biology, 2012, pp. 701-710, vol. 23.
Petitte, J., et al., Avian Pluripotent Stem Cells, Mechanisms of Development, 2004, pp. 1159-1168, vol. 121.
Quziel-Yahalom, et al., Expansion and redifferentiation of adult human pancreatic islet cells, Biochemical and Biophysical Research Communications, Jan. 19, 2006, pp. 291-298, vol. 341.
Ramiya, et al., Reversal of insulin-dependent diabetes using islets generated in vitro from pancreatic stem cells, Nature Medicine, Mar. 2000, pp. 278-282, vol. 6 Issue 3.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, the Journal of Histochemistry and Cytocheinistry, 1986, pp. 527-533, vol. 34 , Issue 4.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Rother, et al., Challenges facing Islet transplantation for the treatment of type 1 diabetes mellitus, the Journal of Clinical Investigation, 2004, pp. 877-883, vol. 114 Issue 7.
Rowely, et al., Meeting Lot-size Challenges of Manufacturing Adherent Cells for Therapy, Bio Process International, Mar. 2012, pp. 16-22, vol. 10 Issue 3.
Schaefer-Graf, et al., Patterns of congenital anomalies and relationship to initial maternal fasting glucose levels in pregnancies com-

(56) References Cited

OTHER PUBLICATIONS plicated by type 2 and gestational diabetes, Am J Obstet Gynecol, 2000, pp. 313-320, vol. 82, Issue 2.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
ThermoFisher Scientific, B-27 Serum-Free Supplement (50x) Liquid, Technical Resources, 2016, URL:https://www.thermofisher.com/nl/en/home/technical-resources/media-formulation.250.html, retrieved from the Internet.
Wachs, et al., High Efficacy of Clonal Growth and Expansion of Adult Neural Stem Cells, Laboratory Investigation, 2003, pp. 949-962, vol. 83, No. 7.
Yadlin, et al., Small-molecule inducers of Insulin expression in pancreatic a-cells, PNAS, Aug. 24, 2010, pp. 15099-15104, vol. 107 Issue 34.
Yang JW, et al., Evaluation of human MSCs cell cycle, viability and differentiation in micromass culture, Biorheology, 2006, pp. 1-2, vol. 43 Issue (3-4).
Yim,et al., Proliferation and differentiation of human embryonic germ cell derivatives in bioactive polymeric fibrous scaffold, J.Biomater.Sci.Polymer Edn, Jan. 19, 2005, pp. 1193-1217, vol. 16 Issue 10.
Zulewski, et al., Multipotentital Neslin-Posltive Stem Cells Iasolated From Adult Pancreatic Islets Differentiate Ex Vivo Into Pancreatic Endocrine, Exocrine, and Hepatic Phenotypes, Diabetes, 2001, pp. 521-533, vol. 50.
Beers, et al., Passaging and Colony Expansion of Human Pluripotent Stem Cells by Enzyme-Free Dissociation in Chemically Defined Culture Conditions, Nature Protocols, 2012, pp. 2029-2040, vol. 7, No. 11.
Chen, et al., Scalable GMP Compliant Suspension Culture System for Human ES Cells, Stem Cell Research, 2012, pp. 388-402, vol. 8.
Guo, et al., Efficient differentiation of insulin-producing cells from skin-derived stem cells, Cell Proliferation, 2009, pp. 49-62, vol. 42.
Maria-Jesus Obregon, Thyroid hormone and adipocyte differentiation, Thyroid, 2008, pp. 185-195, vol. 18, Issue 2.
Olmer, et al., Long Term Expansion of Undifferentiated Human iPS and ES Cells in Suspension Culture Using Defined Medium, Stem Cell Research, 2010, pp. 51-64, vol. 5.
Sjogren-Jansson, et al., Large-Scale Propagation of Four Undifferentiated Human Embryonic Stem Cell Lines in a Feeder-Free Culture System, Developmental Dynamics, Jun. 17, 2005, pp. 1304-1314, vol. 233.
Thomson, Bioprocessing of Embryonic Stem Cells for Drug Discovery, Trends in Biotechnology, 2007, pp. 224-230, vol. 25, No. 5.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Baertschiger, et al., Mesenchymal Stem Cells Derived From Human Exocrine Pancreas Express Transcription Factors Implicated in Beta-Cell Development, Pancreas, 2008, pp. 75-84, vol. 37, No. 1.
Eguizabal, et al., Embryonic Stem Cells/Induced Pluripotent Stem Cells, Complete Meiosis from Human Induced Pluripotent Stem Cells, Stem Cells, 2011, pp. 1186-1195, vol. 29.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Harmon, et al., GDF11 Modulates NGN3+ Islet Progenitor Cell Number and Promotes B-Cell Differentiation in Pancreas Development, Development, 2004, pp. 6163-6174, vol. 131.
Leeper, et al., Stem Cell Therapy for Vascular Regeneration, Adult, Embryonic, and Induced Pluripotent Stem Cells, Circulation, Aug. 3, 2010, pp. 517-526, vol. 122.
Ludwig, et al., Defined Culture Media for Human Embryonic Stem Cells, Embryonic Stem Cells, 2007, pp. 1-16.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2.
Nie, et al., Scalable Passaging of Adherent Human Pluripotent Stem Cells, PLOS One, 2014, pp. 1-9, vol. 9, Issue 1.
Park, et al., Effects of Activin A on Pancreatic Ductal Cells in Streptozotocin-Induced Diabetic Rats, Experimental Transplantation, 2007, pp. 925-930, vol. 83, No. 7.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Richards, et al., Development of Defined Media for the Serum-Free Expansion of Primary Keratinocytes and Human Embryonic Stem Cells, Tissue Engineering, 2008, pp. 221-232, vol. 14, No. 3.
Rowley, et al., Meeting Lot-Size Challenges of Manufacturing Adherent Cells for Therapy, Cell Therapies Manufacturing, 2012, pp. 16-22, vol. 10, No. 3.
Schulz, et al., A Scalable System for Production of Functional Pancreatic Progenitors from Human Embryonic Stem Cells, PLOS One, 2012, pp. 1-17, vol. 7, Issue 5.
Sneddon, et al., Self-Renewal of Embryonic-Stem-Cell-Derived Progenitors by Organ-Matched Mesenchyme, Nature, Nov. 29, 2012, pp. 765-770, vol. 491.
Stacpoole, et al., Efficient Derivation of Neural Precursor Cells, Spinal Motor Neurons and Midbrain Dopaminergic Neurons from Human ES Cells at 3% Oxygen, Nat Protoc, 2012, pp. 1-26, vol. 6, Issue 8.
Vieira, et al., Modulation of Neuronal Stem Cell Differentiation by Hypoxia and Reactive Oxygen Species, Progress in Neurobiology, 2011, pp. 444-455, vol. 93.
Want, et al., Large-Scale Expansion and Exploitation of Pluripotent Stem Cells for Regenerative Medicine Purposes: Beyond the T Flask, Loughborough University Institutional Repository, 2012, pp. 71-84, vol. 7, Issue 1.
Yang, et al., Evaluation of Human MSCs Cell Cycle, Viability and Differentiation in Micromass Culture, Biorheology, 2006, p. 489-496, vol. 43.
Zalzman, et al., Differentiation of Human Liver-Derived, Insulin-Producing Cells Toward the B-Cell Phenotype, Diabetes, 2005, pp. 2568-2575, vol. 54.
Zuscik, et al., Regulation of Chondrogenesis and Chondrocyte Differentiation by Stress, Journal of Clinical Investigation, 2008, pp. 429-438, vol. 118, Issue 2.

\* cited by examiner

METHODS FOR PURIFYING CELLS DERIVED FROM PLURIPOTENT STEM CELLS

CROSS REFERENCE TO RELATED APPLICATION

This application claims priority to provisional application Ser. No. 61/309,193, filed Mar. 1, 2010.

FIELD OF THE INVENTION

The present invention is directed to methods to differentiate pluripotent stem cells. In particular, the present invention provides methods of characterization of cells differentiated into cells expressing markers characteristic of the pancreatic endocrine lineage utilizing unique surface markers. The present invention also provides methods to enrich or sort cells expressing markers characteristic of the pancreatic endocrine lineage. The present invention also provides methods to deplete cells that may contaminate populations of cells expressing markers characteristic of the pancreatic endocrine lineage formed by the methods of the present invention, thereby reducing the incidence of tumor formation in vivo following transplantation.

BACKGROUND

Pluripotent stem cells have the potential to produce differentiated cell types comprising all somatic tissues and organs. Treatment of diabetes using cell therapy is facilitated by the production of large numbers of cells that are able to function similarly to human islets. Accordingly, there is need for producing these cells derived from pluripotent stem cells, as well as reliable methods for purifying such cells.

Proteins and other cell surface markers found on pluripotent stem cell and cell populations derived from pluripotent stem cells are useful in preparing reagents for the separation and isolation of these populations. Cell surface markers are also useful in the further characterization of these cells.

In one example, WO2009131568 discloses a method of purifying a gut endoderm cell comprising: a) exposing a population of cells derived from pluripotent stem cells comprising a gut endoderm cell to a ligand which binds to a cell surface marker expressed on the gut endoderm cell, wherein said cell surface marker is selected from the group consisting of CD49e, CD99, CD165, and CD334; and b) separating the gut endoderm cell from cells derived from pluripotent stem cells which do not bind to the ligand, thereby purifying said gut endoderm cell.

In another example, WO2010000415 discloses the use of an antibody that binds to the antigen TNAP, or functional fragments of the antibody, alone or in combination with an antibody that binds to CD56, or functional fragments of the antibody, for the isolation of stem cells having adipocytic, chondrocytic and pancreatic differentiation potential.

In another example, U.S. Pat. No. 7,371,576 discloses the discovery of a selective cell surface marker that permits the selection of a unique subset of pancreatic stems cells having a high propensity to differentiate into insulin producing cells or into insulin producing cell aggregates.

In another example, U.S. Pat. No. 7,585,672 discloses a method to enrich a culture derived from human embryonic stem cells for cells of endoderm and pancreatic lineages, the method comprising the steps of (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM); (b) culturing the embryoid bodies of step (a) under conditions that permit the embryoid body cells to differentiate into a cell population containing cells of the endoderm and pancreatic lineages; (c) dispersing the cell population of step (b) into single cells; (d) selecting against the expression of SSEA 3/4 positive cells to remove undifferentiated cells from the cells of step (c); (e) selecting against the expression of SSEA-1 positive cells to remove VYS cells from the remaining cells of step (d); and (f) selecting from among the remaining cells of step (e) for the expression of EpCAM positive cells to enrich for cells of endoderm and pancreatic lineages.

U.S. Pat. No. 7,585,672 also discloses a method to enrich a culture derived from human embryonic stem cells for cells of endoderm and pancreatic lineages, the method comprising the steps of (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM); (b) culturing the embryoid bodies of step (a) under conditions that permit the embryoid body cells to differentiate into a cell population containing cells of the endoderm and pancreatic lineages; (c) treating the cell population of step (b) with an effective amount of fibroblast growth factor 10 (FGFl 0); and (d) dispersing the cell population of step (c) into single cells enriched for cells of endoderm and pancreatic lineages (e) selecting against the expression of SSEA-3/4 positive cells to remove undifferentiated stem cells from the cells of step (d); (f) selecting against the expression of SSEA-1 positive cells to remove VYS cells from the cells of step (e); and (g) selecting from among the remaining cells of step (f) for the expression of EpCAM positive cells to enrich for cells of endoderm and pancreatic lineages.

U.S. Pat. No. 7,585,672 also discloses an enrichment method for the creation of a stem cell derived cell population which does not have tumorigenic capability comprising the steps of (a) culturing intact colonies of human embryonic stem cells to form whole, intact embryoid bodies surrounded by visceral yolk sac (VYS) cells, wherein the human embryonic stem cells express Oct-4, surface stage-specific embryonic antigen-3/4 (SSEA 3/4) and epithelial cell adhesion molecule (EpCAM); (b) culturing the embryoid bodies of step (a) under conditions that permit the embryoid body cells to differentiate into a cell population containing cells of the endoderm and pancreatic lineages; (c) dispersing the cell population of step (b) into single cells; (d) selecting against the expression of SSEA 3/4 positive cells to remove undifferentiated cells from the cells of step (c); (e) selecting against the expression of SSEA-1 positive cells to remove VYS cells from the cells of step (d); and (f) selecting from among the remaining cells of step (e) for the expression of EpCAM positive cells, the resulting cells not forming teratomas when injected in immunocompromised mice.

In another example, US20050260749 discloses a method to enrich a culture derived from stem cells for cells of endoderm and pancreatic lineages, the method comprising the steps of culturing stem cells into the formation of embryoid bodies; and selecting among embryoid bodies for the expression of the species appropriate cell surface stage-specific embryonic and culturing only the embryoid bodies which do not express cell surface stage-specific antigen for differentiation into endoderm and pancreatic cells.

In another example, US20100003749 discloses an isolated pancreatic stem cell population, wherein the pancreatic stem cell population is enriched for CD133+CD49f+ pancreatic stem cells.

US20100003749 further discloses the isolation of pancreatic stem cells from primary pancreatic tissue occurs by selecting from a population of pancreatic cells, pancreatic-derived cells, or gastrointestinal-derived cells for cells that are CD133+, CD49f+, or CD133+CD49f+; removing the cells that are CD15+, wherein the remaining cells are CD15−; introducing the remaining cells to a serum-free culture medium containing one or more growth factors; and proliferating the remaining cells in the culture medium.

In another example, Dorrell et at state: "We have developed a novel panel of cell-surface markers for the isolation and study of all major cell types of the human pancreas. Hybridomas were selected after subtractive immunization of Balb/C mice with intact or dissociated human islets and assessed for cell-type specificity and cell-surface reactivity by immunohistochemistry and flow cytometry. Antibodies were identified by specific binding of surface antigens on islet (panendocrine or α-specific) and nonislet pancreatic cell subsets (exocrine and duct). These antibodies were used individually or in combination to isolate populations of α, β, exocrine, or duct cells from primary human pancreas by FACS and to characterize the detailed cell composition of human islet preparations. They were also employed to show that human islet expansion cultures originated from nonendocrine cells and that insulin expression levels could be increased to up to 1% of normal islet cells by subpopulation sorting and overexpression of the transcription factors Pdx-1 and ngn3, an improvement over previous results with this culture system. These methods permit the analysis and isolation of functionally distinct pancreatic cell populations with potential for cell therapy." (*Stem Cell Research*, Volume 1, Issue 3, September 2008, Pages 155-156).

In another example, Sugiyama et al state: "We eventually identified two antigens, called CD133 and CD49f, useful for purifying NGN3+ cells from mice. CD133 (also called prominin-1) is a transmembrane protein of unknown function and a known marker of haematopoietic progenitor and neural stem cells. CD49f is also called α6-integrin, and a receptor subunit for laminin. By combining antibodies that recognize CD133 and CD49f, we fractionated four distinct pancreatic cell populations. Immunostaining and RT-PCR revealed that the CD49fhigh CD133+ cell population ('fraction I', 50% of input) comprised mainly differentiated exocrine cells that express CarbA. The CD49flow CD133− fraction ('fraction III', 10% of input) included hormone+ cells expressing endocrine products like insulin and glucagon. By contrast, the CD49flow CD133+ fraction (called 'fraction II', 13% of input) contained NGN3+ cells, but not hormone+ cells. Approximately 8% of fraction II cells produced immunostainable NGN3. In the CD49f−CD133− fraction ('fraction IV', 25% of input), we did not detect cells expressing NGN3, CarbA or islet hormones." (*Diabetes, Obesity and Metabolism*, Volume 10, Issue s4, Pages 179-185).

In another example, Fujikawa et al state: "When CD45−TER119− side-scatterlow GFPhigh cells were sorted, α-fetoprotein-positive immature endoderm-characterized cells, having high growth potential, were present in this population. Clonal analysis and electron microscopic evaluation revealed that each single cell of this population could differentiate not only into hepatocytes, but also into biliary epithelial cells, showing their bilineage differentiation activity. When surface markers were analyzed, they were positive for Integrin-α6 and -β1, but negative for c-Kit and Thy1.1." (*Journal of Hepatlogy*, Vol 39, pages 162-170).

In another example, Zhao et al state: "In this study, we first identified N-cadherin as a surface marker of hepatic endoderm cells for purification from hES cell-derivates, and generated hepatic progenitor cells from purified hepatic endoderm cells by co-culture with murine embryonic stromal feeders (STO) cells. These hepatic progenitor cells could expand and be passaged for more than 100 days. Interestingly, they co-expressed the early hepatic marker AFP and biliary lineage marker KRT7, suggesting that they are a common ancestor of both hepatocytes and cholangiocytes. Moreover, these progenitor cells could be expanded extensively while still maintaining the bipotential of differentiation into hepatocyte-like cells and cholangiocyte-like cells, as verified by both gene expression and functional assays. Therefore, this work offers a new in vitro model for studying liver development, as well as a new source for cell therapy based on hepatic progenitors." (PLoS ONE 4(7): e6468. doi:10.1371/journal.pone.0006468).

In another example, Cai et at state: "To further increase the PDX1+ cell purity, we sorted the activin A-induced cells using CXCR4 . . . , a marker for ES cell-derived endodermal cells. Sorting with CXCR4 enriched the endodermal cell population because nearly all the cells in the CXCR4+ population were positive for the endodermal cell marker SOX17, and >90% of the cells were positive for FOXA2." (*Journal of Molecular Cell Biology* Advance Access originally published online on Nov. 12, 2009. Journal of Molecular Cell Biology 2010 2(1):50-60; doi:10.1093/jmcb/mjp037).

In another example, Koblas et at state: "We found that population of human CD133− positive pancreatic cells contains endocrine progenitors expressing neurogenin-3 and cells expressing human telomerase, ABCG2, Oct-3/4, Nanog, and Rex-1, markers of pluripotent stem cells. These cells were able to differentiate into insulin-producing cells in vitro and secreted C-peptide in a glucose-dependent manner. Based on our results, we suppose that the CD133 molecule represents another cell surface marker suitable for identification and isolation of pancreatic endocrine progenitors". (*Transplant Proc.* 2008 March; 40(2):415-8)

In another example, Sugiyama et al state: "we found CD133 was expressed by NGN3+ cells. CD133 appeared to be localized to the apical membrane of pancreatic ductal epithelial cells." (*PNAS* 2007 104:175-180; published online before print Dec. 26, 2006, doi:10.1073/pnas.0609490104).

In another example, Kobayashi et al state: "The embryonic pancreatic epithelium, and later the ductal epithelium, is known to give rise to the endocrine and exocrine cells of the developing pancreas, but no specific surface marker for these cells has been identified. Here, we utilized Dolichos Biflorus Agglutinin (DBA) as a specific marker of these epithelial cells in developing mouse pancreas. From the results of an immunofluorescence study using fluorescein-DBA and pancreatic specific cell markers, we found that DBA detects specifically epithelial, but neither differentiating endocrine cells nor acinar cells. We further applied this marker in an immunomagnetic separation system (Dynabead system) to purify these putative multi-potential cells from a mixed developing pancreatic cell population. This procedure could be applied to study differentiation and cell lineage selections in the developing pancreas, and also may be applicable to selecting pancreatic precursor cells for potential cellular engineering." (*Biochemical and Biophysical Research Communications*, Volume 293, Issue 2, 3 May 2002, Pages 691-697).

Identification of markers expressed by cells derived from pluripotent stem cells would expand the understanding of these cells, aid in their identification in vivo and in vitro, and would enable their positive enrichment in vitro for study and use. Thus, there remains a need for tools that are useful in isolating and characterizing cells derived from pluripotent stem cells, in particular, cells expressing markers characteristic of the pancreatic endocrine lineage.

SUMMARY

In one embodiment, the present invention provides a method to differentiate a population of pluripotent stem cells into a population of cells expressing markers characteristic of the pancreatic endocrine lineage, comprising the steps of:
 a. Culturing a population of pluripotent stem cells,
 b. Differentiating the population of pluripotent stem cells into a population of cells expressing markers characteristic of the definitive endoderm lineage,
 c. Differentiating the population of cells expressing markers characteristic of the definitive endoderm lineage into cells expressing markers characteristic of the primitive gut tube lineage,
 d. Differentiating the population of cells expressing markers characteristic of the primitive gut tube lineage into a population of cells expressing markers characteristic of the pancreatic endoderm lineage, and
 e. Differentiating the population of cells expressing markers characteristic of the pancreatic endoderm lineage into a population cells expressing markers characteristic of the pancreatic endocrine lineage.

In one embodiment, the population of cells expressing markers characteristic of the pancreatic endocrine lineage is transplanted into an animal, wherein the cells expressing markers characteristic of the pancreatic endocrine lineage form insulin producing cells. In one embodiment, the efficiency of the formation of insulin producing cells is enhanced by enriching the population for cells expressing markers characteristic of the pancreatic endocrine lineage prior to transplantation.

In one embodiment, the efficiency of the formation of insulin producing cells is determined by measuring the time taken for the expression of C-peptide to reach detectable levels following transplantation.

In an alternate embodiment, the enrichment decreases the ability of the transplanted cells to form teratomas following transplantation.

DETAILED DESCRIPTION

Figure 1:
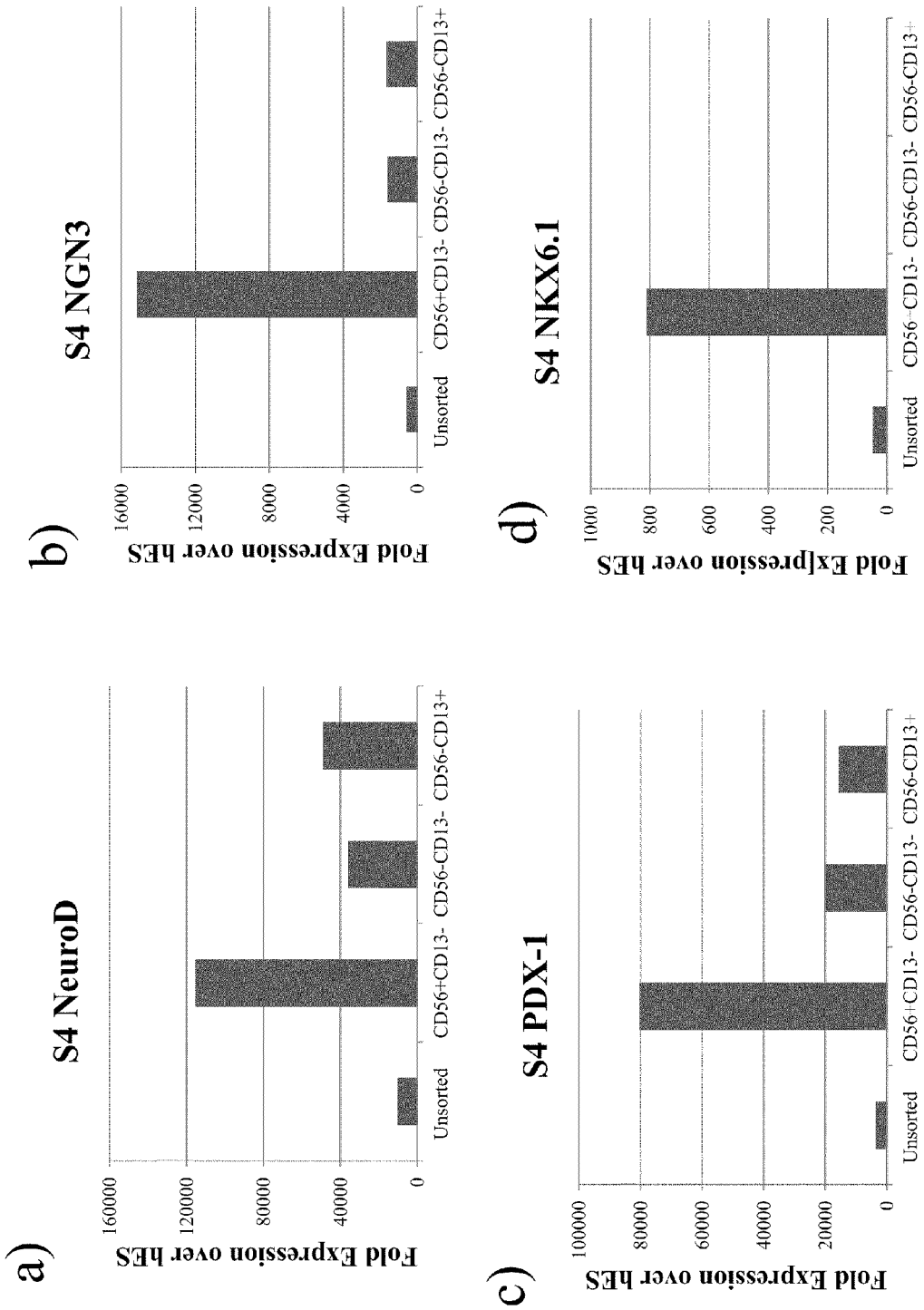
FIG. 1 shows the expression of NEUROD (panel a), NGN3 (panel b), PDX1 (panel c), NKX6.1 (panel d), NKX2.2 (panel e), and PAX4 (panel f) in populations of $CD56^+CD13^-$, $CD56^-CD13^-$ and $CD56^-CD13^+$ cells, as detected via real-time PCR. Fold expression is shown relative to undifferentiated H1 embryonic stem cells.
Figure 1:
Figure 1:
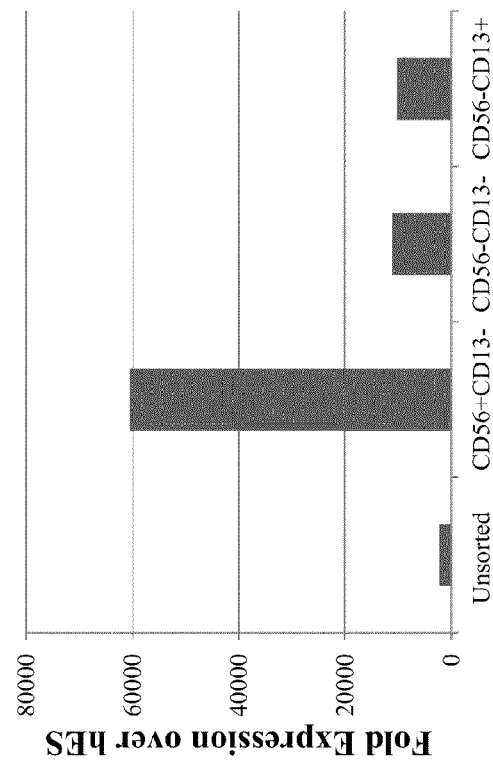

For clarity of disclosure, and not by way of limitation, the detailed description of the invention is divided into the following subsections that describe or illustrate certain features, embodiments or applications of the present invention.

Definitions

"β-cell lineage" refers to cells with positive gene expression for the transcription factor PDX-1 and at least one of the following transcription factors: NGN3, NKX2.2, NKX6.1, NEUROD, ISL1, HNF-3 beta, MAFA, PAX4, and PAX6. Cells expressing markers characteristic of the β cell lineage include β cells.

"Cells expressing markers characteristic of the definitive endoderm lineage" as used herein refers to cells expressing at least one of the following markers: SOX17, GATA4, HNF-3 beta, GSC, CER1, Nodal, FGF8, Brachyury, Mix-like homeobox protein, FGF4, CD48, eomesodermin (EOMES), DKK4, FGF17, GATA6, CD184, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the primitive gut tube lineage" refers to cells expressing at least one of the following markers: HNF-1 beta, or HNF-4 alpha.

"Cells expressing markers characteristic of the pancreatic endoderm lineage" as used herein refers to cells expressing at least one of the following markers: PDX1, HNF-1 beta, PTF-1 alpha, HNF6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NUN-3, NEUROD, ISL1, PDX1, NKX6.1, PAX4, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: CD184, HNF-3 beta, GATA4, SOX17, Cerberus, OTX2, goosecoid, c-Kit, CD99, and Mixl1.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Pancreatic endocrine cell" or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF8.

"Primitive streak cell" as used herein refers to a cell expressing at least one of the following markers: Brachyury, Mix-like homeobox protein, or FGF4.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (i) totipotent, meaning able to give rise to all embryonic and extraembryonic cell types; (ii) pluripotent, meaning able to give rise to all embryonic cell types; (iii) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (iv) oligopotent, meaning able to give rise to a more restricted subset of cell lineages than multipotent stem cells; and (v) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. Dedifferentiation refers to the process by which a cell reverts to a less specialized (or committed) position within the lineage of a cell. As used herein, the lineage of a cell defines the heredity of the cell, that is, which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

Various terms are used to describe cells in culture. "Maintenance" refers generally to cells placed in a growth medium under conditions that facilitate cell growth and/or division that may or may not result in a larger population of the cells. "Passaging" refers to the process of removing the cells from one culture vessel and placing them in a second culture vessel under conditions that facilitate cell growth and/or division.

A specific population of cells, or a cell line, is sometimes referred to or characterized by the number of times it has been passaged. For example, a cultured cell population that has been passaged ten times may be referred to as a P10 culture. The primary culture, that is, the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (that is, the number of population doublings) during the period between passaging depends on many factors, including but not limited to the seeding density, substrate, medium, growth conditions, and time between passaging.

Enrichment of Cells Expressing Markers Characteristic of the Pancreatic Endocrine Lineage In one embodiment, the present invention provides a method to differentiate a population of pluripotent stem cells into a population of cells expressing markers characteristic of the pancreatic endocrine lineage, comprising the steps of:
   a. Culturing a population of pluripotent stem cells,
   b. Differentiating the population of pluripotent stem cells into a population of cells expressing markers characteristic of the definitive endoderm lineage,
   c. Differentiating the population of cells expressing markers characteristic of the definitive endoderm lineage into cells expressing markers characteristic of the primitive gut tube lineage,
   d. Differentiating the population of cells expressing markers characteristic of the primitive gut tube lineage into a population of cells expressing markers characteristic of the pancreatic endoderm lineage, and
   e. Differentiating the population of cells expressing markers characteristic of the pancreatic endoderm lineage into a population cells expressing markers characteristic of the pancreatic endocrine lineage.

In one embodiment, the population of cells expressing markers characteristic of the pancreatic endocrine lineage is transplanted into an animal, wherein the cells expressing markers characteristic of the pancreatic endocrine lineage form insulin producing cells. In one embodiment, the efficiency of the formation of insulin producing cells is enhanced by enriching the population for cells expressing markers characteristic of the pancreatic endocrine lineage prior to transplantation.

In one embodiment, the efficiency of the formation of insulin producing cells is determined by measuring the time taken for the expression of C-peptide to reach detectable levels following transplantation.

In an alternate embodiment, the enrichment decreases the ability of the transplanted cells to form teratomas following transplantation.

Cells expressing markers of the pancreatic endocrine lineage are identified or selected through the binding of antigens, found on the surfaces of the cells, to reagents that specifically bind the cell surface antigen.

In an alternate embodiment, cells expressing markers characteristic of the pancreatic endocrine lineage are further differentiated into insulin producing cells, prior to transplantation into an animal. Insulin producing cells are identified or selected through the binding of antigens, found on the surfaces of the cells, to reagents that specifically bind the cell surface antigen.

In an alternate embodiment, the present invention provides a method to differentiate a population of pluripotent stem cells into a population of cells expressing markers characteristic of the pancreatic endocrine lineage, comprising the steps of:
   a. Culturing a population of pluripotent stem cells,
   b. Differentiating the population of pluripotent stem cells into a population of cells expressing markers characteristic of the definitive endoderm lineage,
   c. Differentiating the population of cells expressing markers characteristic of the definitive endoderm lineage into cells expressing markers characteristic of the primitive gut tube lineage,
   d. Enriching the population of cells that express markers characteristic of the primitive gut tube lineage,
   e. Differentiating the population of cells expressing markers characteristic of the primitive gut tube lineage into a population of cells expressing markers characteristic of the pancreatic endoderm lineage, and
   f. Differentiating the population of cells expressing markers characteristic of the pancreatic endoderm lineage into a population cells expressing markers characteristic of the pancreatic endocrine lineage.

In one embodiment, the population of cells expressing markers characteristic of the pancreatic endocrine lineage is transplanted into an animal, wherein the cells expressing markers characteristic of the pancreatic endocrine lineage form insulin producing cells. In one embodiment, the efficiency of the formation of insulin producing cells is enhanced by enriching the population of cells that express markers characteristic of the primitive gut tube lineage prior to transplantation.

Cells expressing markers of the primitive gut tube lineage are identified or selected through the binding of antigens, found on the surfaces of the cells, to reagents that specifically bind the cell surface antigen.

Surface Antigens that Facilitate Enrichment of Cells Expressing Markers Characteristic of the Pancreatic Endocrine Lineage In one embodiment, prior to transplantation into an animal, the population of cells expressing markers characteristic of the pancreatic endocrine lineage is treated with at least one reagent that is capable of binding to a marker selected from the group consisting of CD9, CD13, CD15, CD47, CD56, CD73, CD117, CD133, CD184, CD200, CD318, CD326 and SSEA4.

In one embodiment, treatment with the at least one reagent results in a population of cells expressing markers characteristic of the pancreatic endocrine lineage that are positive for the expression of the marker CD56 and negative for the expression of the marker CD13.

In one embodiment, treatment with the at least one reagent results in a population of cells expressing markers characteristic of the pancreatic endocrine lineage that are positive for the expression of the marker CD56 and negative for the expression of the marker CD15.

In one embodiment, treatment with the at least one reagent results in a population of cells expressing markers characteristic of the pancreatic endocrine lineage that are negative for the expression of the marker CD133.

In one embodiment, treatment with the at least one reagent results in a population of cells expressing markers characteristic of the pancreatic endocrine lineage that are negative for the expression of the marker CD15.

In one embodiment, treatment with the at least one reagent results in a population of cells expressing markers characteristic of the pancreatic endocrine lineage that are positive for the expression of the marker CD184.

In one embodiment, treatment with the at least one reagent results in a population of cells expressing markers characteristic of the pancreatic endocrine lineage that are negative for the expression of the marker SSEA4.

Surface Antigens that Facilitate Enrichment of
Insulin Producing Cells

In one embodiment, prior to transplantation into an animal, the population of cells expressing markers characteristic of the pancreatic endocrine lineage is further differentiated into a population of insulin producing cells. The population of insulin producing cells is treated with at least one reagent that is capable of binding to a marker selected from the group consisting of CD47, CD56, CD57 CD98 and SSEA4.

In one embodiment, treatment with the at least one reagent results in a population of insulin producing cells that are positive for the expression of the marker CD56 and CD57. Alternatively, the population of insulin producing cells may be positive for the expression of CD98. Alternatively, the population of insulin producing cells may be negative for the expression of CD47.

In one embodiment, treatment with the at least one reagent results in a population of insulin producing cells that are negative for the expression of the marker SSEA4.

CD13 is expressed on the majority of peripheral blood monocytes and granulocytes. It is also expressed by the majority of acute myeloid leukemias, chronic myeloid leukemias in myeloid blast crisis, a smaller percentage of lymphoid leukemias and myeloid cell lines. CD13 is also found in several types of non hematopoietic cells such as fibroblasts and endothelial cells and in a soluble form in blood plasma. CD13 is not expressed on B cells, T cells, platelets or erythrocytes. CD13 plays a role in biologically active peptide metabolism, in the control of growth and differentiation, in phagocytosis and in bactericidal/tumoricidal activities. CD13 also serves as a receptor for human coronaviruses (HCV).

CD15 is a carbohydrate adhesion molecule that can be expressed on glycoproteins, glycolipids and proteoglycans. CD15 mediates phagocytosis and chemotaxis, found on neutrophils; expressed in patients with Hodgkin disease, some B-cell chronic lymphocytic leukemias, acute lymphoblastic leukemias, and most acute nonlymphocytic leukemias. It is also called Lewis x and SSEA-1 (stage specific embryonic antigen 1) and represents a marker for murine pluripotent stem cells, in which it plays an important role in adhesion and migration of the cells in the preimplantation embryo.

CD47 is a membrane protein, which is involved in the increase in intracellular calcium concentration that occurs upon cell adhesion to extracellular matrix. The protein is also a receptor for the C-terminal cell binding domain of thrombospondin, and it may play a role in membrane transport and signal transduction.

CD56, also known as Neural Cell Adhesion Molecule (NCAM) is a homophilic binding glycoprotein expressed on the surface of neurons, glia, skeletal muscle and natural killer cells. NCAM has been implicated as having a role in cell-cell adhesion, neurite outgrowth, synaptic plasticity, and learning and memory.

CD57 also known as HNK-1 or Leu-7, is an antigenic oligosaccharide moiety detected on extracellular proteins of certain cell types. In blood, CD57 is found on 15-20% of mononuclear cells, including subsets of NK and T cells, though not on erythrocytes, monocytes, granulocytes, or platelets. Also, CD57 expression can be found on a variety of neural cell types.

CD98 is a glycoprotein that comprises the light subunit of the Large neutral Amino acid Transporter (LAT1). LAT1 is a heterodimeric membrane transport protein that preferentially transports neutral branched (valine, leucine, isoleucine) and aromatic (tryptophan, tyrosine) amino acids.

CD133 is a glycoprotein also known in humans and rodents as Prominin 1 (PROM1). It is a member of pentaspan transmembrane glycoproteins (5-transmembrane, 5-TM), which specifically localizes to cellular protrusions. CD133 is expressed in hematopoietic stem cells, endothelial progenitor cells, glioblastomas, neuronal and glial stem cells. See Corbeil et al, *Biochem Biophys Res Commun* 285 (4): 939-44, 2001. doi:10.1006/bbrc.2001.5271. PMID 11467842.

Surface Antigens that Facilitate Enrichment of
Cells Expressing Markers Characteristic of the
Primitive Gut Tube Lineage In an alternate embodiment, the present invention provides a method to differentiate a population of pluripotent stem cells into a population of cells expressing markers characteristic of the pancreatic endocrine lineage, comprising the steps of:
a. Culturing a population of pluripotent stem cells,
b. Differentiating the population of pluripotent stem cells into a population of cells expressing markers characteristic of the definitive endoderm lineage,
c. Differentiating the population of cells expressing markers characteristic of the definitive endoderm lineage into cells expressing markers characteristic of the primitive gut tube lineage,
d. Enriching the population of cells that express markers characteristic of the primitive gut tube lineage,
e. Differentiating the population of cells expressing markers characteristic of the primitive gut tube lineage into a population of cells expressing markers characteristic of the pancreatic endoderm lineage, and
f. Differentiating the population of cells expressing markers characteristic of the pancreatic endoderm lineage into a population cells expressing markers characteristic of the pancreatic endocrine lineage.

In one embodiment, the population of cells expressing markers characteristic of the pancreatic endocrine lineage is transplanted into an animal, wherein the cells expressing markers characteristic of the pancreatic endocrine lineage form insulin producing cells. In one embodiment, the efficiency of the formation of insulin producing cells is enhanced by enriching the population of cells that express markers characteristic of the primitive gut tube lineage prior to transplantation.

The population of cells that express markers characteristic of the primitive gut tube lineage is treated with at least one reagent that is capable of binding to the LIF receptor.

The cells expressing markers characteristic of the pancreatic endocrine lineage, cells expressing markers characteristic of the primitive gut tube lineage, or insulin producing cells may be enriched, depleted, isolated, separated, sorted and/or purified as further described in the examples. As used herein, the terms "enriched" or "purified" or enriched or purified due to depletion of other known cell populations, indicate that the cells has been subject to some selection process so that the population is enriched and/or purified. Also, the subject cells are also considered relatively enriched and/or purified, i.e. there is significantly more of a particular differentiated cell population as compared to another cell population, or as compared to pluripotent stem cells before "enrichment" or "purification", or as compared to the original or initial cell culture.

Enriching or purifying for a given differentiated cell type may involve "depleting" or "separating" or "sorting" one or more known cell types from another cell type. In one embodiment, a population of cells may be purified by depleting an unwanted differentiated cell type. It may be advantageous to enrich and purify a cell expressing markers characteristic of the pancreatic endocrine lineage by depleting the culture of known or unknown cell types. In this way, the enriched or purified cell population would not have the bound or attached antibody. Because there is no need to remove the antibody from the purified population, the use of the enriched or purified cells for cell therapies may be improved.

Methods for enriching, depleting, isolating, separating, sorting and/or purifying may include, for example, selective culture conditions, wherein the culture conditions are detrimental to any undesirable cell types.

Methods for enriching, depleting, isolating, separating, sorting and/or purifying may also include, for example, antibody-coated magnetic beads, affinity chromatography and "panning" with antibody attached to a solid matrix or solid phase capture medium, e.g. plate, column or other convenient and available technique. Techniques providing accurate separation include flow cytometry methods which are useful for measuring cell surface and intracellular parameters, as well as shape change and granularity and for analyses of beads used as antibody- or probe-linked reagents. Readouts from flow cytometry assays include, but are not limited to, the mean fluorescence associated with individual fluorescent antibody-detected cell surface molecules or cytokines, or the average fluorescence intensity, the median fluorescence intensity, the variance in fluorescence intensity, or some relationship among these.

In some aspects of embodiments with analytical steps involving flow cytometry, minimal parameters or characteristics of the beads are scatter (FS and/or SS) and at least one fluorescent wavelengths. Flow cytometry can be used to quantitate parameters such as the presence of cell surface proteins or conformational or posttranslational modification thereof; intracellular or secreted protein, where permeabilization allows antibody (or probe) access, and the like. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000.

The staining intensity of cells may be monitored by flow cytometry, where lasers detect the quantitative levels of fluorochrome (which is proportional to the amount of cell surface marker bound by specific reagents, e.g. antibodies). Flow cytometry, or FACS, may also be used to separate cell populations based on the intensity of binding to a specific reagent, as well as other parameters such as cell size and light scatter. Although the absolute level of staining can differ with a particular fluorochrome and reagent preparation, the data can be normalized to a control. In order to normalize the distribution to a control, each cell is recorded as a data point having a particular intensity of staining In order to normalize the distribution to a control, each cell is recorded as a data point having a particular intensity of staining. These data points may be displayed according to a log scale, where the unit of measure is arbitrary staining intensity. In one example, the brightest cells in a population are designated as 4 logs more intense than the cells having the lowest level of staining. When displayed in this manner, it is clear that the cells falling in the highest log of staining intensity are bright, while those in the lowest intensity are negative. The "low" staining cells, which fall in the 2-3 log of staining intensity, may have properties that are unique from the negative and positive cells. An alternative control may utilize a substrate having a defined density of marker on its surface, for example a fabricated bead or cell line, which provides the positive control for intensity. The "low" designation indicates that the level of staining is above the brightness of an isotype matched control, but is not as intense as the most brightly staining cells normally found in the population.

The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. For example, a negative designation indicates that the level of staining is at or below the brightness of an isotype matched negative control; whereas a dim designation indicates that the level of staining can be near the level of a negative stain, but can also be brighter than an isotype matched control.

Identifiers of individual cells, for example different cell types or cell type variants, may be fluorescent, as for example labeling of different unit cell types with different levels of a fluorescent compound, and the like as described herein above. In some aspects of embodiments where two cell types are to be mixed, one is labeled and the other not. In some aspects of embodiments where three or more cell types are to be included, each cell type may labeled to different levels of fluorescence by incubation with different concentrations of a labeling compound, or for different times. As identifiers of large numbers of cells, a matrix of fluorescence labeling intensities of two or more different fluorescent colors may be used, such that the number of distinct unit cell types that are identified is a number of fluorescent levels of one color, e.g., carboxyfluorescein succinimidyl ester (CFSE), times the number of fluorescence levels employed of the second color, e.g. tetramethylrhodamine isothiocyanate (TRITC), or the like, times the number of levels of a third color, etc. Alternatively, intrinsic light scattering properties of the different cell types, or characteristics of the BioMAPs of the test parameters included in the analysis, may be used in addition to or in place of fluorescent labels as unit cell type identifiers.

In another aspect, cells may be enriched, depleted, separated, sorted and/or purified using conventional affinity or antibody techniques. For example, the ligand and/or antibody may be conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like.

In one embodiment, the ligand, agent, and/or antibodies described herein may be directly or indirectly conjugated to a magnetic reagent, such as a super-paramagnetic microparticle (microparticle). Direct conjugation to a magnetic particle may be achieved by use of various chemical linking groups, as known in the art. In some embodiments, the antibody is coupled to the microparticles through side chain amino or sufhydryl groups and heterofunctional cross-linking reagents.

A large number of heterofunctional compounds are available for linking to entities. For example, at least, 3-(2- pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle can be used. An example of a magnetic separation device is described in WO 90/07380, PCT/US96/00953, and EP 438,520, incorporated herein by reference in its entirety.

The purified cell population may be collected in any appropriate medium. Suitable media may include, for example, Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), and StemPro®hESC SFM.

In one embodiment, the cells expressing markers characteristic of the pancreatic endocrine lineage are enriched by treatment with at least one agent that selects cells that do not express markers characteristic of the pancreatic endocrine lineage. In an alternate embodiment, the cells expressing markers characteristic of the pancreatic endocrine lineage are enriched by treatment with at least one agent that selects for insulin-producing cells.

Using the methods described herein, cell populations or cell cultures may be enriched in cell content by at least about 2- to about 1000-fold as compared to untreated cell populations or cell cultures. In some embodiments, cells expressing markers characteristic of the pancreatic endocrine lineage may be enriched by at least about 5- to about 500-fold as compared to untreated cell populations or cell cultures. In other embodiments, cells expressing markers characteristic of the pancreatic endocrine lineage may be enriched from at least about 10- to about 200-fold as compared to untreated cell populations or cell cultures. In still other embodiments, cells expressing markers characteristic of the pancreatic endocrine lineage may be enriched from at least about 20- to about 100-fold as compared to untreated cell populations or cell cultures. In yet other embodiments, cells expressing markers characteristic of the pancreatic endocrine lineage may be enriched from at least about 40- to about 80-fold as compared to untreated cell populations or cell cultures. In certain embodiments, cells expressing markers characteristic of the pancreatic endocrine lineage may be enriched from at least about 2- to about 20-fold as compared to untreated cell populations or cell cultures.

Characterization of Cells Derived from Pluripotent Stem Cells

The formation of differentiated cells from pluripotent stem cells may be determined by determining the expression of markers characteristic of a given differentiated cell type. In some embodiments, the identification and characterization of a differentiated cell is by expression of a certain marker or different expression levels and patterns of more than one marker.

Specifically, the presence or absence, the high or low expression, of one or more the marker(s) can typify and identify a cell-type. Also, certain markers may have transient expression, whereby the marker is highly expressed during one stage of development and poorly expressed in another stage of development. The expression of certain markers can be determined by measuring the level at which the marker is present in the cells of the cell culture or cell population as compared to a standardized or normalized control marker. In such processes, the measurement of marker expression can be qualitative or quantitative. One method of quantitating the expression of markers that are produced by marker genes is through the use of quantitative PCR (Q-PCR). Methods of performing Q-PCR are well known in the art. Other methods which are known in the art can also be used to quantitate marker gene expression. For example, the expression of a marker gene product can be detected by using antibodies specific for the marker gene product of interest (e.g. Western blot, flow cytometry analysis, and the like). In certain embodiments, the expression of marker genes characteristic of differentiated cells as well as the lack of significant expression of marker genes characteristic of differentiated cells may be determined.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers listed in this disclosure can be obtained from public databases such as GenBank.

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra 1-60, and Tra 1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.). Undifferentiated pluripotent stem cells also typically express OCT4 and TERT, as detected by RT-PCR.

Markers characteristic of the pancreatic endoderm lineage are selected from the group consisting of PDX1, HNF1 beta, PTF1 alpha, HNF6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Markers characteristic of the definitive endoderm lineage are selected from the group consisting of SOX17, GATA4, HNF3 beta, GSC, CERT, Nodal, FGF8, Brachyury, Mix-like homeobox protein, FGF4, CD48, eomesodermin (EOMES), DKK4, FGF17, GATA6, CD184, C-Kit, CD99, and OTX2. Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Markers characteristic of the pancreatic endocrine lineage are selected from the group consisting of NGN3, NEUROD, ISL1, PDX1, NKX6.1, PAX4, NGN3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone-expressing cell. Alternatively, the pancreatic endocrine cell may be a pancreatic hormone-secreting cell.

In one aspect of the present invention, the pancreatic endocrine cell is a cell expressing markers characteristic of the β cell lineage. A cell expressing markers characteristic of the β cell lineage expresses PDX1 and at least one of the following transcription factors: NGN3, NKX2.2, NKX6.1, NEUROD, ISL1, HNF3 beta, MAFA, PAX4, and PAX6. In one aspect of the present invention, a cell expressing markers characteristic of the β cell lineage is a β cell.

Pluripotent Stem Cells

Characterization of Pluripotent Stem Cells

Pluripotent stem cells may express one or more of the stage-specific embryonic antigens (SSEA) 3 and 4, and markers detectable using antibodies designated Tra-1-60 and Tra-1-81 (Thomson et al., Science 282:1145 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde and then developing with Vector Red as a substrate, as described by the manufacturer (Vector Laboratories, Burlingame Calif.). Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

Sources of Pluripotent Stem Cells

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells, as well as a pluripotent stem cell population already cultured in the presence of feeder cells. Also suitable are mutant human embryonic stem cell lines, such as, for example, BG01v (BresaGen, Athens, Ga.). Also suitable are cells derived from adult human somatic cells, such as, for examples, cells disclosed in Takahashi et al, Cell 131: 1-12 (2007).

In one embodiment, human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Also contemplated, are pluripotent stem cells that are derived from somatic cells. In one embodiment, pluripotent stem cells suitable for use in the present invention may be derived according to the methods described in Takahashi et at (Cell 126: 663-676, 2006).

In an alternate embodiment, pluripotent stem cells suitable for use in the present invention may be derived according to the methods described in Li et at (Cell Stem Cell 4: 16-19, 2009).

In an alternate embodiment, pluripotent stem cells suitable for use in the present invention may be derived according to the methods described in Maherali et at (Cell Stem Cell 1: 55-70, 2007).

In an alternate embodiment, pluripotent stem cells suitable for use in the present invention may be derived according to the methods described in Stadtfeld et at (Cell Stem Cell 2: 230-240).

In an alternate embodiment, pluripotent stem cells suitable for use in the present invention may be derived according to the methods described in Nakagawa et at (Nature Biotechnology 26: 101-106, 2008).

In an alternate embodiment, pluripotent stem cells suitable for use in the present invention may be derived according to the methods described in Takahashi et at (Cell 131: 861-872, 2007).

In an alternate embodiment, pluripotent stem cells suitable for use in the present invention may be derived according to the methods described in U.S. patent application Ser. No. 61/256,149, assigned to Centocor R&D, Inc.

Culture of Pluripotent Stem Cells

In one embodiment, pluripotent stem cells are cultured on a layer of feeder cells or extracellular matrix protein that support the pluripotent stem cells in various ways, prior to culturing according to the methods of the present invention. For example, pluripotent stem cells are cultured on a feeder cell layer that supports proliferation of pluripotent stem cells without undergoing substantial differentiation. The growth of pluripotent stem cells on a feeder cell layer without differentiation is supported using (i) Obtaining a culture vessel containing a feeder cell layer; and (ii) a medium conditioned by culturing previously with another cell type, or a non-conditioned medium, for example, free of serum or even chemically defined.

In another example, pluripotent stem cells are cultured in a culture system that is essentially free of feeder cells, but nonetheless supports proliferation of pluripotent stem cells without undergoing substantial differentiation. The growth of pluripotent stem cells in feeder-cell free culture without differentiation is supported using (i) an adlayer on a solid substrate surface with one or more extracellular matrix proteins; and (ii) a medium conditioned by culturing previously with another cell type, or a non-conditioned medium, for example, free of serum or even chemically defined.

In an alternate embodiment, pluripotent stem cells are cultured on a surface modified plate containing from at least about 0.5% N, a sum of O and N of greater than or equal to 17.2% and a contact angle of at least about 13.9 degrees in a medium conditioned by culturing previously with another cell type, or a non-conditioned medium, for example, free of serum or even chemically defined.

Culture medium: An example of cell culture medium suitable for use in the present invention may be found in US20020072117. Another example of cell culture medium suitable for use in the present invention may be found in U.S. Pat. No. 6,642,048. Another example of cell culture medium suitable for use in the present invention may be found in WO2005014799. Another example of cell culture medium suitable for use in the present invention may be found in Xu et al (Stem Cells 22: 972-980, 2004). Another example of cell culture medium suitable for use in the present invention may be found in US20070010011. Another example of cell culture medium suitable for use in the present invention may be found in Cheon et al. (BioReprod DOI:10.1095/biolreprod.105.046870; 19 Oct. 2005). Another example of cell culture medium suitable for use in the present invention may be found in Levenstein et al. (Stem Cells 24: 568-574, 2006). Another example of cell culture medium suitable for use in the present invention may be found in US20050148070. Another example of cell culture medium suitable for use in the present invention may be found in US20050233446. Another example of cell culture medium suitable for use in the present invention may be found in U.S. Pat. No. 6,800,480. Another example of cell culture medium suitable for use in the present invention may be found in US20050244962. Another example of cell culture medium suitable for use in the present invention may be found in WO2005065354. Another example of cell culture medium suitable for use in the present invention may be found in WO2005086845.

Suitable culture media may also be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

Differentiation of Pluripotent Stem Cells

In one embodiment, pluripotent stem cells are propagated in culture and then treated in a manner that promotes their differentiation into another cell type. For example, pluripotent stem cells formed using the methods of the present invention may be differentiated into neural progenitors or cardiomyocytes according to the methods disclosed in WO2007030870.

In another example, pluripotent stem cells formed using the methods of the present invention may be differentiated into hepatocytes according to the methods disclosed in U.S. Pat. No. 6,458,589.

Differentiation of Pluripotent Stem Cells Formed Using the Methods of the Present Invention into Cells Expressing Markers Characteristic of the Definitive Endoderm Lineage Pluripotent stem cells formed using the methods of the present invention may be differentiated into cells expressing markers characteristic of the definitive endoderm lineage by any method in the art.

For example, pluripotent stem cells formed using the methods of the present invention may be differentiated into cells expressing markers characteristic of the definitive endoderm lineage according to the methods disclosed in D'Amour et al, Nature Biotechnology 23, 1534-1541 (2005).

For example, pluripotent stem cells formed using the methods of the present invention may be differentiated into cells expressing markers characteristic of the definitive endoderm lineage according to the methods disclosed in Shinozaki et al, Development 131, 1651-1662 (2004).

For example, pluripotent stem cells formed using the methods of the present invention may be differentiated into cells expressing markers characteristic of the definitive endoderm lineage according to the methods disclosed in McLean et al, Stem Cells 25, 29-38 (2007).

For example, pluripotent stem cells formed using the methods of the present invention may be differentiated into cells expressing markers characteristic of the definitive endoderm lineage according to the methods disclosed in D'Amour et al, Nature Biotechnology 24, 1392-1401 (2006).

In another example, pluripotent stem cells formed using the methods of the present invention may be differentiated into cells expressing markers characteristic of the definitive endoderm lineage according to the methods disclosed in U.S. patent application Ser. No. 11/736,908, assigned to LifeScan, Inc.

In another example, pluripotent stem cells formed using the methods of the present invention may be differentiated into cells expressing markers characteristic of the definitive endoderm lineage according to the methods disclosed in U.S. patent application Ser. No. 11/779,311, assigned to LifeScan, Inc.

In another example, pluripotent stem cells formed using the methods of the present invention may be differentiated into cells expressing markers characteristic of the definitive endoderm lineage according to the methods disclosed in U.S. patent application Ser. No. 12/493,741, assigned to LifeScan, Inc.

In another example, pluripotent stem cells formed using the methods of the present invention may be differentiated into cells expressing markers characteristic of the definitive endoderm lineage according to the methods disclosed in U.S. patent application Ser. No. 12/494,789, assigned to LifeScan, Inc.

Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

Differentiation of Pluripotent Stem Cells Formed Using the Methods of the Present Invention into Cells Expressing Markers Characteristic of the Pancreatic Endoderm Lineage Pluripotent stem cells formed using the methods of the present invention may be differentiated into cells expressing markers characteristic of the pancreatic endoderm lineage by any method in the art.

For example, pluripotent stem cells may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with a fibroblast growth factor and the hedgehog signaling pathway inhibitor KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in Nature Biotechnology 24, 1392-1401 (2006).

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with retinoic acid one fibroblast growth factor for a period of time, according to the methods disclosed in U.S. patent application Ser. No. 11/736,908, assigned to LifeScan, Inc.

For example, cells expressing markers characteristic of the definitive endoderm lineage obtained according to the methods of the present invention are further differentiated into cells expressing markers characteristic of the pancreatic endoderm lineage, by treating the cells expressing markers characteristic of the definitive endoderm lineage with retinoic acid (Sigma-Aldrich, MO) and exendin 4, then removing the medium containing DAPT (Sigma-Aldrich, MO) and exendin 4 and subsequently culturing the cells in medium containing exendin 1, IGF-1 and HGF. An example of this method is disclosed in Nature Biotechnology 24, 1392-1401 (2006).

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing DAPT (Sigma-Aldrich, MO) and exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/990,529, assigned to LifeScan, Inc.

Differentiation of Pluripotent Stem Cells Formed Using the Methods of the Present Invention into Cells Expressing Markers Characteristic of the Pancreatic Endocrine Lineage Pluripotent stem cells formed using the methods of the present invention may be differentiated into cells expressing markers characteristic of the pancreatic endocrine lineage by any method in the art.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4, then removing the medium containing exendin 4 and subsequently culturing the cells in medium containing exendin 1, IGF-1 and HGF. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing DAPT (Sigma-Aldrich, MO) and exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by culturing the cells expressing markers characteristic of the pancreatic endoderm lineage in medium containing exendin 4. An example of this method is disclosed in D'Amour et al, Nature Biotechnology, 2006.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/736,908, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 11/779,311, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/953,178, assigned to LifeScan, Inc.

For example, cells expressing markers characteristic of the pancreatic endoderm lineage obtained according to the methods of the present invention are further differentiated into cells expressing markers characteristic of the pancreatic endocrine lineage, by treating the cells expressing markers characteristic of the pancreatic endoderm lineage with a factor that inhibits the Notch signaling pathway, according to the methods disclosed in U.S. patent application Ser. No. 60/990,529, assigned to LifeScan, Inc.

The present invention is further illustrated, but not limited by, the following examples.

EXAMPLES

Example 1

Differentiation of Human Embryonic Stem Cells of the Cell Line H1 to Pancreatic Endocrine Cells in the Absence of Fetal Bovine Serum Cells of the human embryonic stem cells line H1 at various passages (p40 to p52) were cultured on MATRIGEL (1:30 dilution) coated dishes and differentiated into pancreatic lineages using a multi-step protocol as follows:

a. Stage I (Definitive Endoderm): Human embryonic stem cells were cultured in RPMI medium supplemented with 2% fatty acid-free BSA (Catalog #68700, Proliant, IA), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day. Cells were then treated with RPMI medium supplemented with 2% BSA and 100 ng/ml activin A plus 8 ng/ml of bFGF for an additional two days, then b. Stage II (Primitive gut tube): Cells were treated with RPMI+2% fatty acid-free BSA and 50 ng/ml FGF7 and 0.25 µM SANT-1 (#S4572, Sigma, MO), for two to three days, then c. Stage III (Posterior foregut): Cells were treated with DMEM/High-Glucose supplemented with 1:200 dilution of ITS-X (Invitrogen, CA) and 0.1% BSA (Lipid Rich) (Invitrogen, Ca No. 11021-045), 50 ng/ml FGF7, 0.25 µM SANT-1, 2 µM Retinoic acid (RA) (Sigma, MO), 100 ng/ml of Noggin (R & D Systems, MN), and Activin A at 20 ng/ml for four days; In certain variations, Noggin was replaced with the AMPK inhibitor 6-[4-(2-Piperidin-1-ylethoxy)phenyl]-3-pyridin-4-ylpyrazolo[1,5-a]pyrimidine (Sigma, No. P5499) at a concentration of 2 µM. In yet other variations, a P38 inhibitor (4-[4-(4-Fluorophenyl)-1-(3-phenylpropyl)-5-pyridin-4-yl-1H-imidazol-2-yl]but-3-yn-1-ol) (disclosed in U.S. Pat. No. 6,521,655) was added at 2.5 µM, then d. Stage IV (Pancreatic endocrine precursor): Cells were treated with DMEM/High-Glucose supplemented with 1:200 dilution of ITS-X (Invitrogen, CA) and 0.1% BSA (Invitrogen, Ca), 100 ng/ml Noggin, 1 µM ALK5 inhibitor (SD-208, disclosed in Molecular Pharmacology 2007 72:152-161) for three days, then e. Stage V (Pancreatic endocrine cells): Cell were treated with DMEM/High-Glucose supplemented with 1:200 dilution of ITS-X (Invitrogen, CA), 0.1% BSA (Invitrogen, Ca), 1 µM ALK5 inhibitor II (Catalog #616452, Calbiochem, Ca) for seven days, then f. Stage VI (Mature Pancreatic endocrine cells): Cells were treated with DMEM/High-Glucose supplemented with 1:200 dilution of ITS-X (Invitrogen, CA), 0.1% BSA (Invitrogen, Ca) for seven days, with media changes every other day.

Example 2

Flow Cytometric Characterization and Sorting of Enriched Various Pancreatic Cell Lineages To facilitate the isolation and characterization of novel cell populations form various stages of the differentiation process outlined in Example 1, a detailed characterization of the cells obtained from the various stages was done by flow cytometry. A complete list of antibodies used and the expression levels of surface markers at various stages of differentiation is shown in Table I.

Cells of the human embryonic stem cell line H1 at various passages (p40 to p52) were cultured on MATRIGEL-coated plates, and differentiated into pancreatic endocrine cells using the protocol described in Example 1.

Cells at different stages of maturation (posterior foregut (Stage III), endocrine precursor cells (Stage IV), pancreatic endocrine cells (Stage V) or mature pancreatic endocrine cells (Stage VI) were gently released by incubation in TrypLE Express (Invitrogen #12604, CA) for 2-3 minutes at 37° C. and washed twice in BD FACS staining buffer containing 2% BSA (BD #554657, CA). Approximately 0.5-1×10$^6$ cells were re-suspended in 100-200 µl blocking buffer (0.5% human gamma-globulin diluted 1:4 in staining buffer (BD, CA) for staining. For staining with directly conjugated primary antibodies, the appropriate antibody was added to the cells at a final dilution of 1:20, and cells and incubated for 30 min at 4° C. For unconjugated antibodies, primary antibodies were added to cells at 1:50-1:100 dilution and cells incubated for 30 min at 4° C. followed two washes in staining buffer. Cells were then incubated in the appropriate secondary antibodies at 1:500 dilution. Stained cells were re-suspended in 300 μl staining buffer and 5-10 μl of 7AAD added for live/dead cell discrimination prior to analysis on the BD FACS Canto II.

For cell sorting, approximately 30-40 million cells were similarly processed as for flow cytometric analysis. Cells were stained with the appropriate antibodies as shown in Table II. Cells were sorted either into two or three sub-populations as summarized in Table II. Cell sorting gates were established based on the isotype matched controls. An aliquot of sorted cells were analyzed for purity following the sorting followed by PCR analysis for expression of key pancreatic markers. RNA was collected using the Rneasy Mini Kit, Qiagen, CA) was collected from presort sample, and the various fractions.

Cell surface markers used for sorting were selected based on the expression of various markers in populations of cells analyzed at different stages of the differentiation protocol outlined in Example 1. The markers employed in this study are disclosed in Table II. Briefly, the surface markers disclosed in Table II were used either singly or in combination to sort various populations of cells. Samples of the sorted cells were taken to analyze the expression of markers characteristic of the pancreatic endocrine lineage by real-time PCR.

Sorting of Cells Expressing Markers Characteristic of the Pancreatic Endocrine Lineage Antibodies to CD56 and CD13 were used to sort a population of cells obtained from Stage IV of the differentiation protocol outlined in Example 1. Three populations of cells were identified: a) $CD56^+CD13^-$, b) $CD56^-CD13^-$ and c) $CD56^-CD13^+$ populations of cells. The $CD56^+CD13^-$ population was enriched approximately 1.3 fold following sorting, and the sorted cells were highly enriched for the expression of markers characteristic of the pancreatic endocrine lineage, including NEUROD, NGN3, PDX1, NKX6.1, NKX2.2 and PAX-4, when compared to unsorted cells at stage IV, or populations of $CD56^-CD13^-$ cells, or populations of $CD56^-CD13^+$ cells. See FIG. 1, panels a-f.

Figure 2:
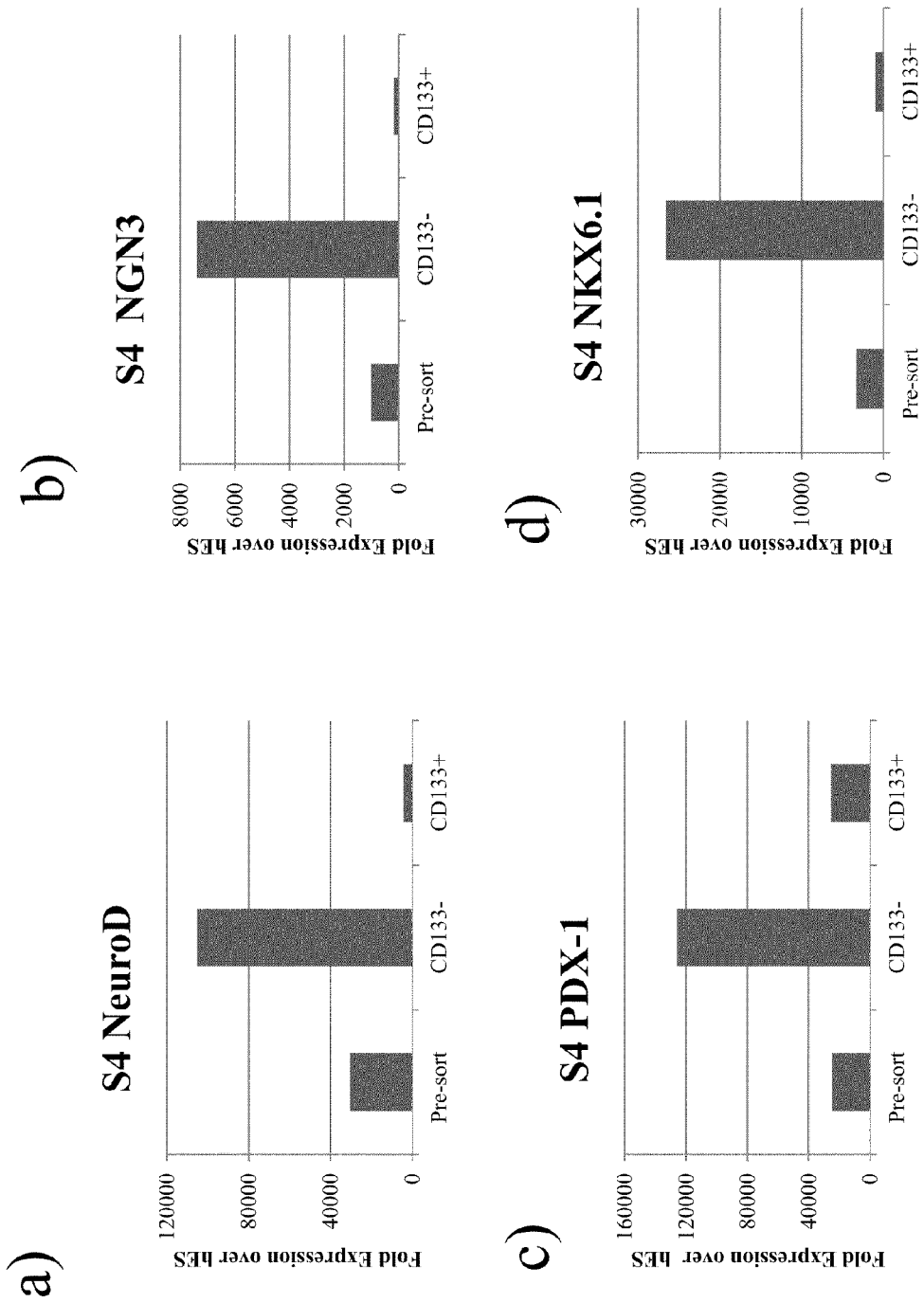
FIG. 2 shows the expression of NEUROD (panel a), NGN3 (panel b), PDX1 (panel c), NKX6.1 (panel d), NKX2.2 (panel e), and PAX4 (panel f), as detected via real-time PCR, in populations of cells sorted using an antibody to CD133. Fold expression is shown relative to undifferentiated H1 embryonic stem cells.
Figure 2:
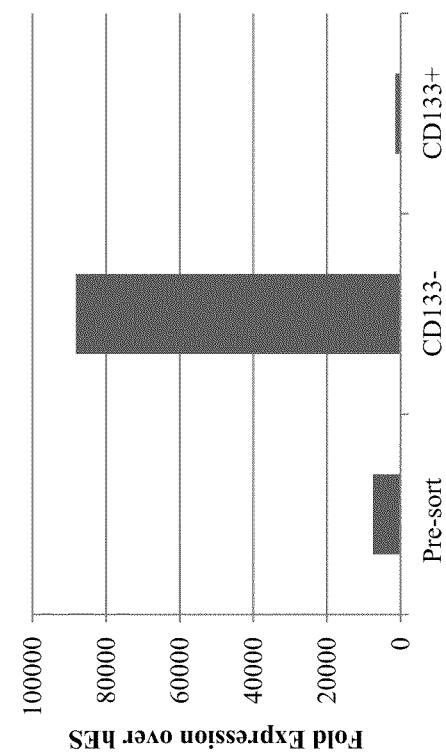
Figure 2:
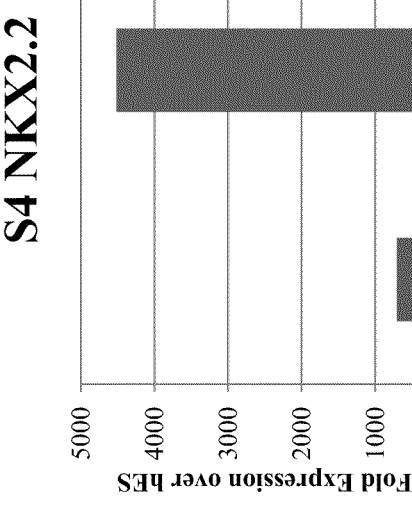

In a second series of experiments, antibodies to CD133 were used to sort a population of cells obtained from Stage IV of the differentiation protocol outlined in Example 1. Two populations of cells were identified: a) $CD133^+$, and b) $CD133^-$ populations of cells. The $CD133^-$ population was enriched approximately 1.9 fold following sorting, and the sorted cells were highly enriched for the expression of markers characteristic of the pancreatic endocrine lineage, including NEUROD, NGN3, PDX1, NKX6.1, NKX2.2 and PAX-4, when compared to unsorted cells at stage IV, or populations of $CD133^+$ cells. See FIG. 2, panels a-f.

Figure 3:
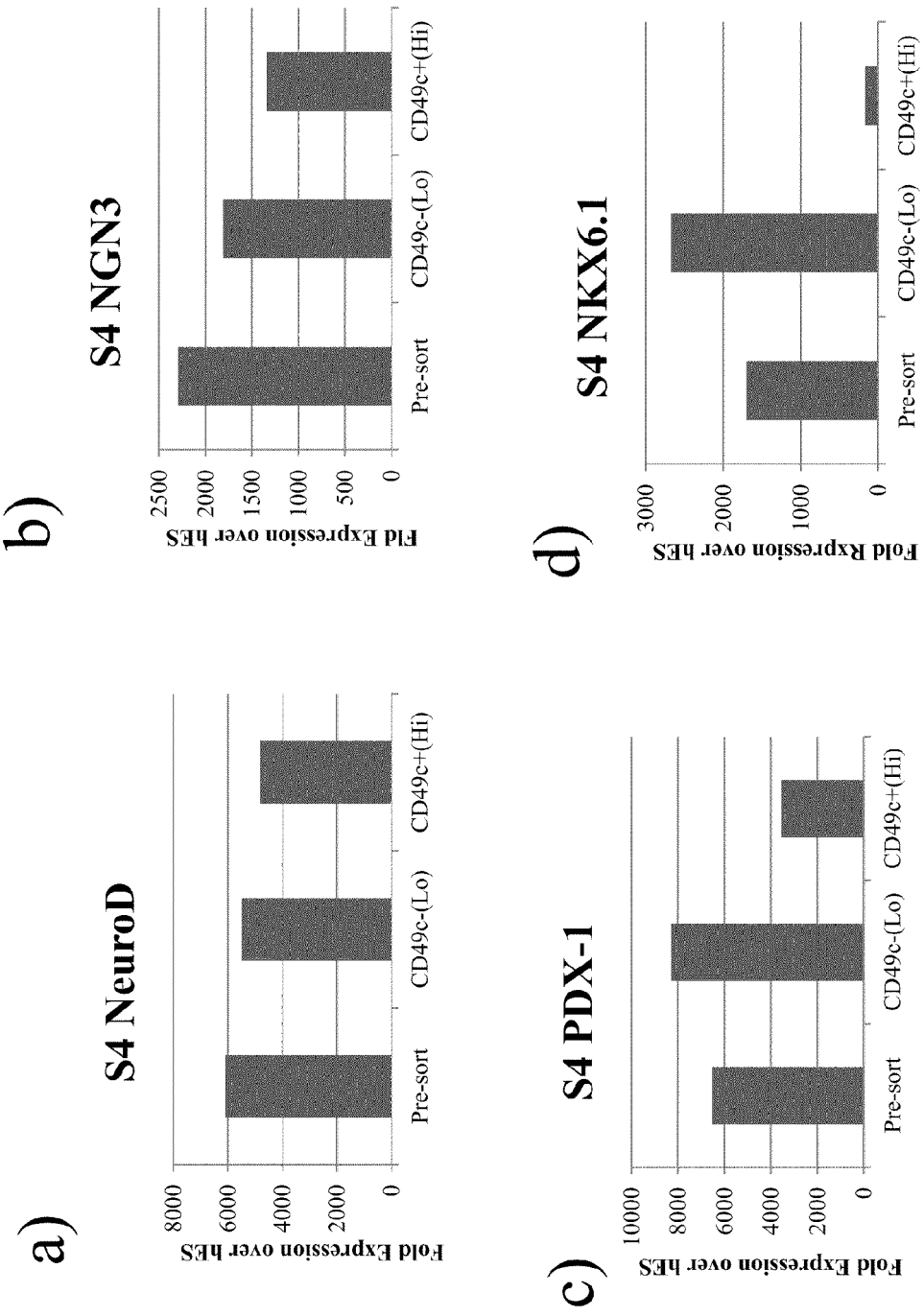
FIG. 3 shows the expression of NEUROD (panel a), NGN3 (panel b), PDX1 (panel c), and NKX6.1 (panel d), as detected via real-time PCR, in populations of cells sorted using an antibody to CD49c. Fold expression is shown relative to undifferentiated H1 embryonic stem cells.

In a third series of experiments, antibodies to CD49c were used to sort a population of cells obtained from Stage IV of the differentiation protocol outlined in Example 1. Two populations of cells were identified: a) $CD49c^{HI}$, and b) $CD49c^{LO}$ populations of cells. $CD49c^{LO}$ cells were enriched approximately 3.1 fold following sorting, and the sorted cells were highly enriched for the expression of markers characteristic of the pancreatic endocrine lineage, including NEUROD, NGN3, PDX1, and NKX6.1 when compared to unsorted cells or $CD49c^{HI}$ cells. See FIG. 3, panels a-d.

Figure 4:
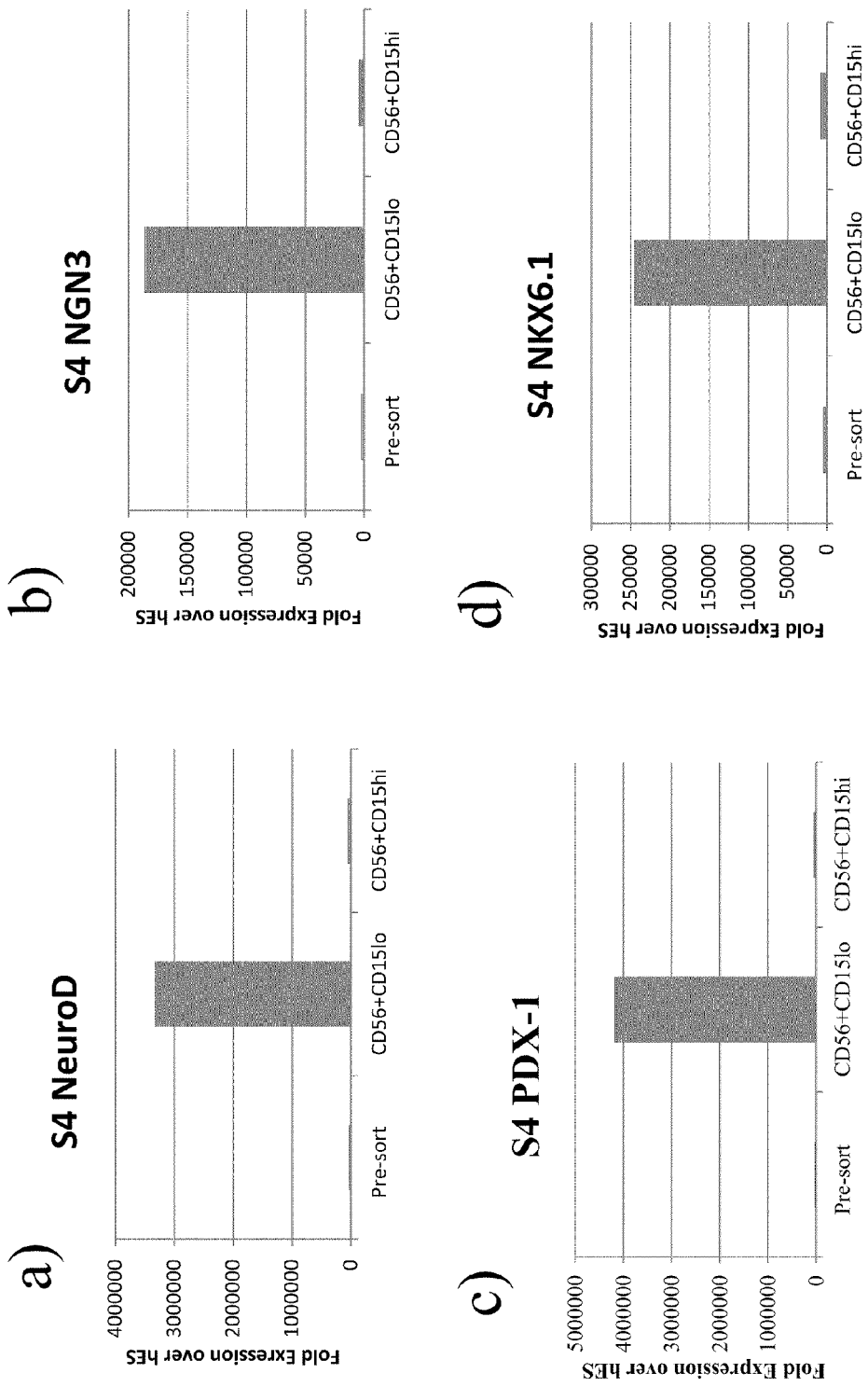
FIG. 4 shows the expression of NEUROD (panel a), NGN3 (panel b), PDX1 (panel c), NKX6.1 (panel d), insulin (panel e), and glucagon (panel f), as detected via real-time PCR, in populations of cells sorted using antibodies to CD56 and CD15. Fold expression is shown relative to undifferentiated H1 embryonic stem cells.
Figure 4:
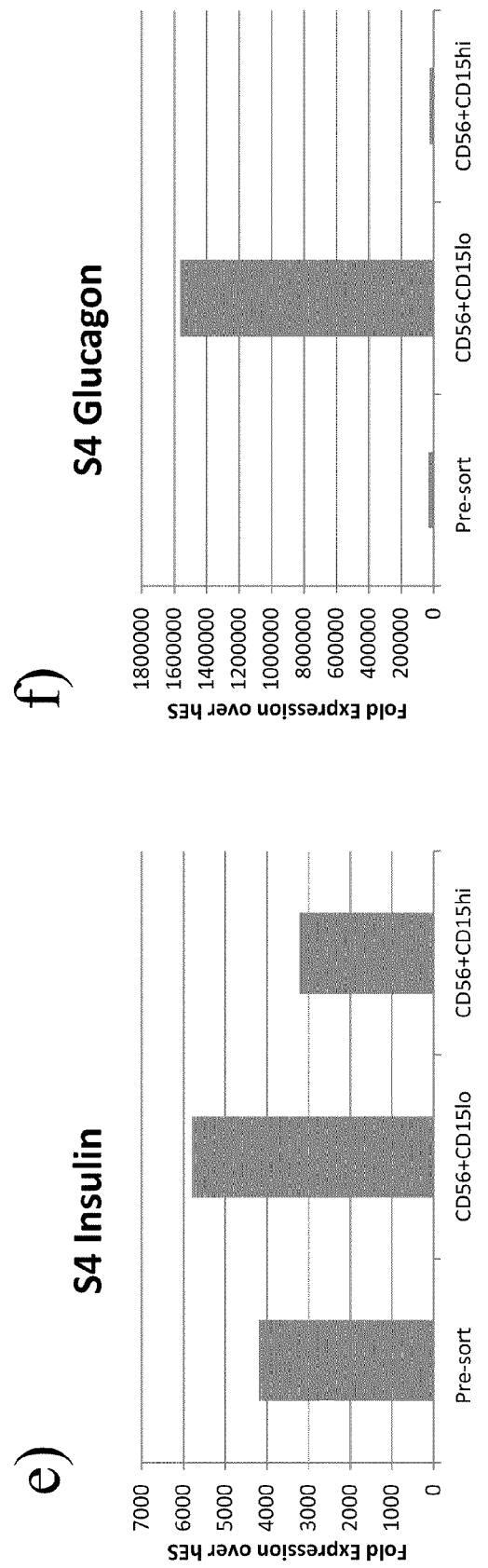
Figure 5:
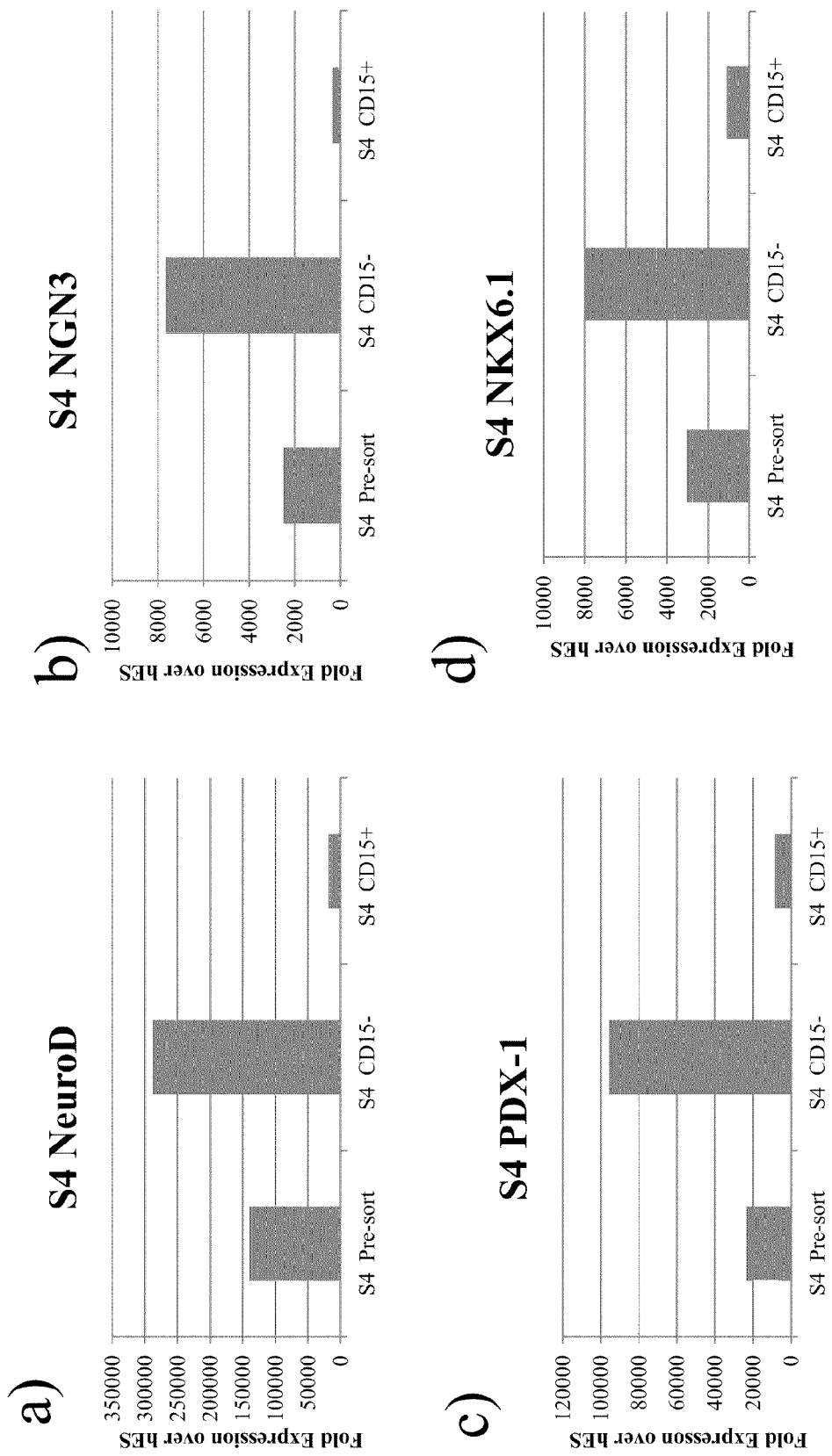
FIG. 5 shows the expression of NEUROD (panel a), NGN3 (panel b), PDX1 (panel c), NKX6.1 (panel d), NKX2.2 (panel e), PAX-4 (panel f), glucagon (panel g) and insulin (panel h) as detected via real-time PCR, in populations of cells sorted using an antibody to CD15. Fold expression is shown relative to undifferentiated H1 embryonic stem cells.
Figure 5:
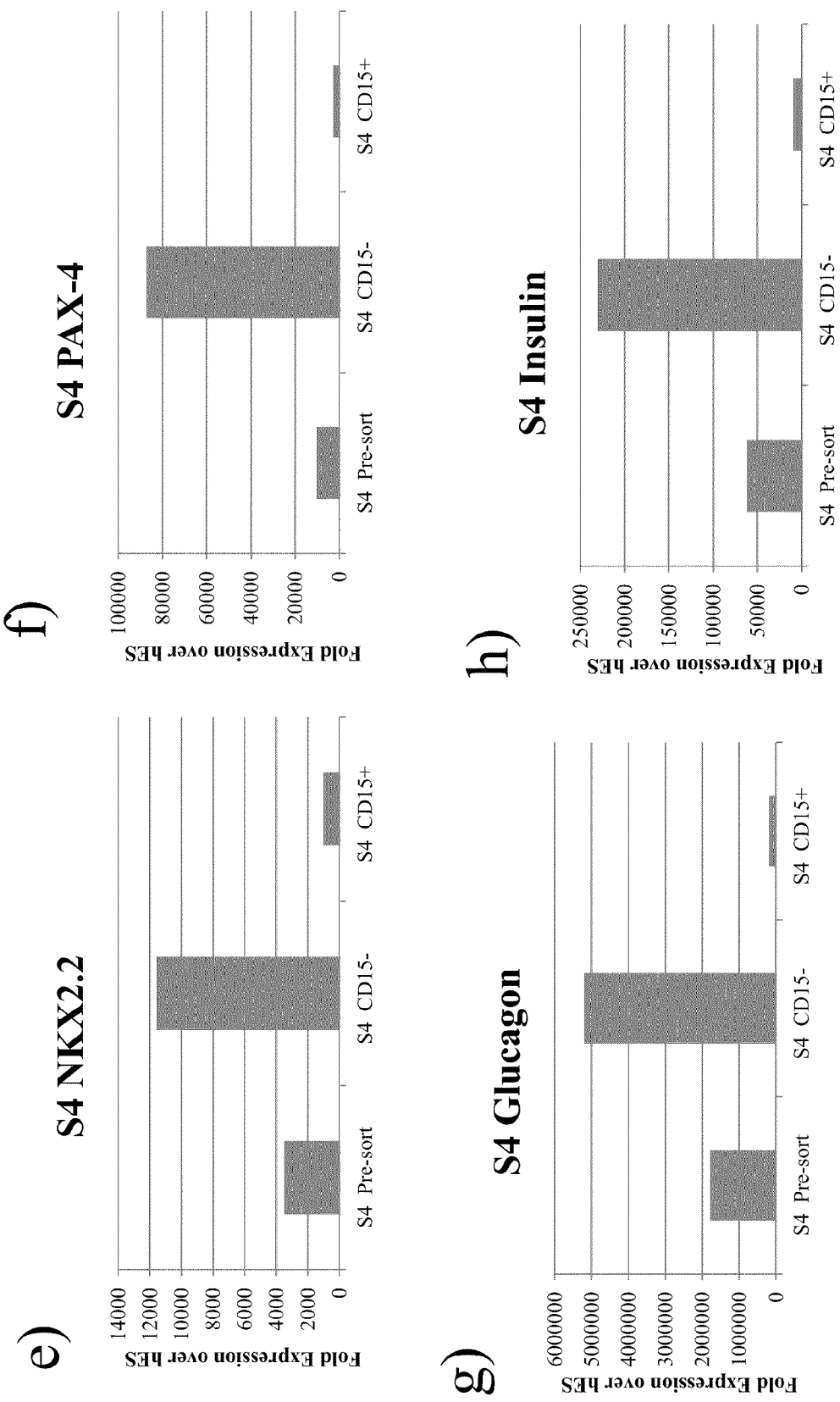

In a fourth series of experiments, antibodies to CD56 and CD15 were used to sort a population of cells obtained from Stage IV of the differentiation protocol outlined in Example 1. The following populations of cells were identified: a) $CD56^+CD15^{LO}$, b) $CD56^+CD15^{HI}$, c) $CD15^+$ and d) $CD15^-$ populations of cells. Populations of $CD15^-$ cells were enriched approximately 1.1 fold following sorting. Populations of $CD56^+CD15^{lo}$ cells were highly enriched for the expression of markers characteristic of the pancreatic endocrine lineage including NEUROD, NGN3, PDX1, NKX6.1, Insulin and glucagon compared to unsorted cells, or populations of $CD56^+CD15^{hi}$ cells. See FIG. 4, panels a-f. Similarly, populations of $CD15^-$ cells sorted using a single marker were highly enriched for the expression of markers characteristic of the pancreatic endocrine lineage including NEUROD, NGN3, PDX1, NKX6.1, NKX2.2, PAX-4, glucagon and insulin, when compared to unsorted cells or populations of $CD15^+$ cells. See FIG. 5, panels a-h.

Figure 6:
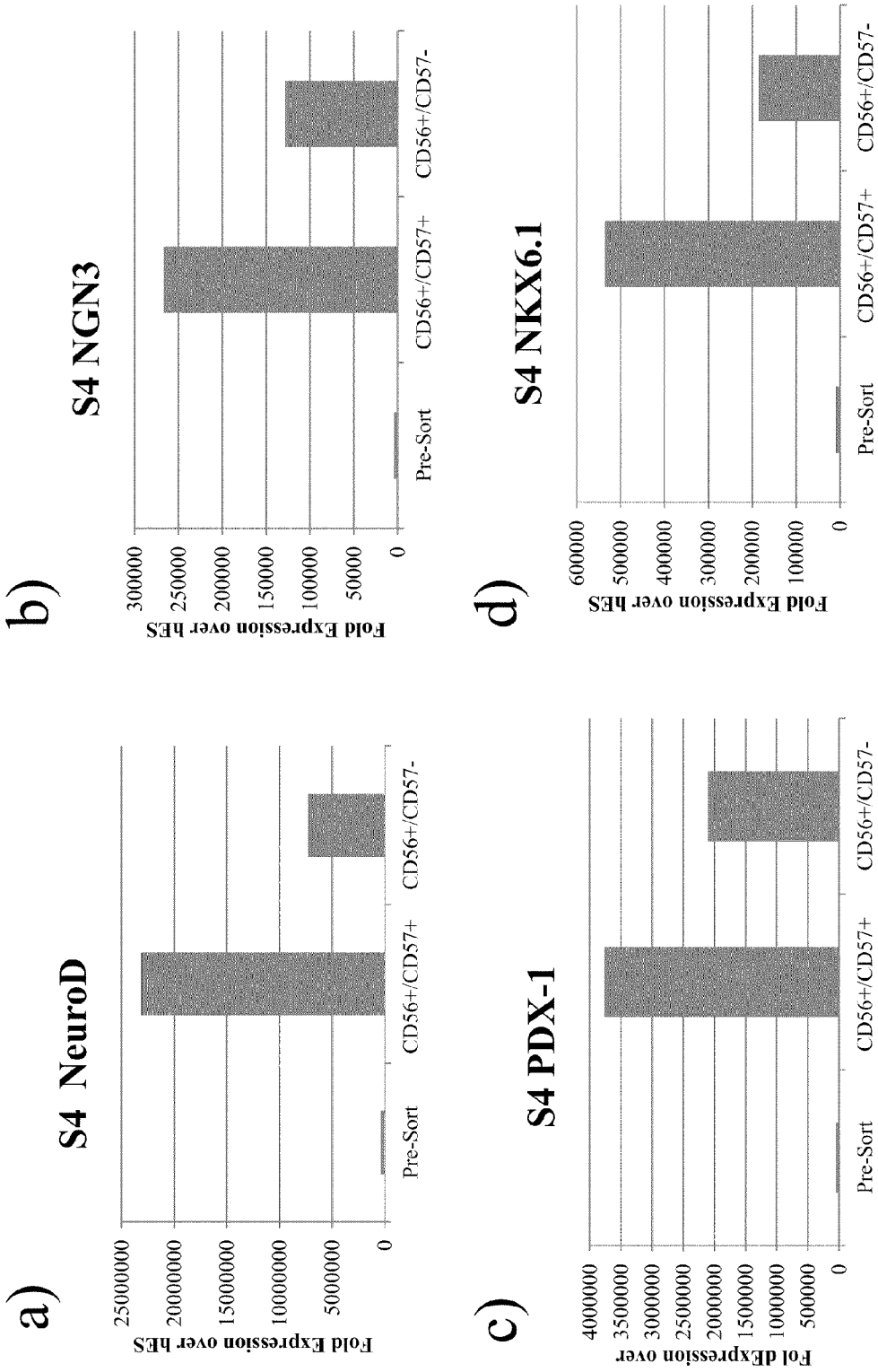
FIG. 6 shows the expression of NEUROD (panel a), NGN3 (panel b), PDX1 (panel c), NKX6.1 (panel d), NKX2.2 (panel e), insulin (panel f), and glucagon (panel g) as detected via real-time PCR, in populations of cells sorted using antibodies to CD56 and CD57. Fold expression is shown relative to undifferentiated H1 embryonic stem cells.
Figure 6:
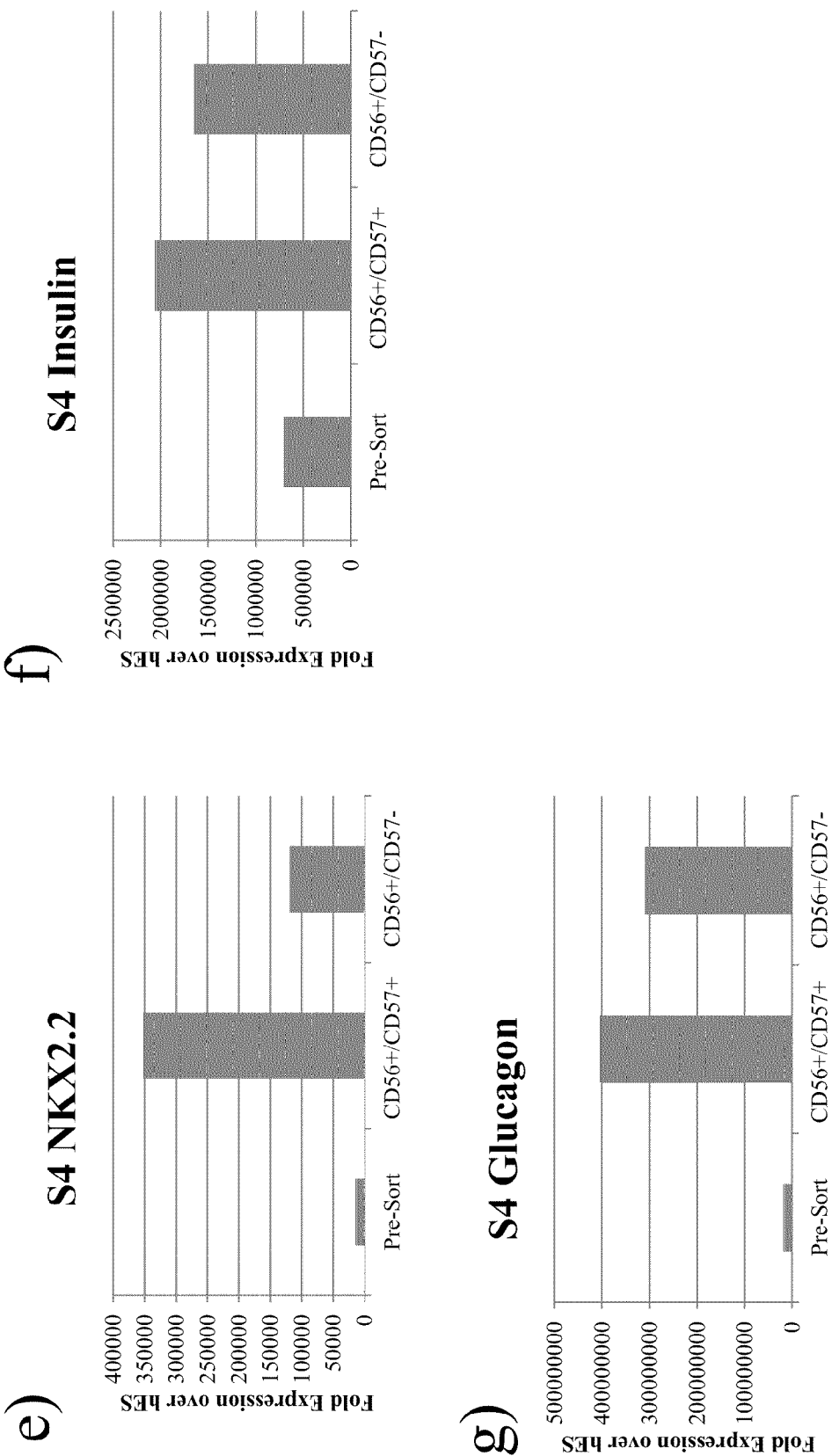

In a fifth series of experiments, antibodies to CD56 and CD57 were used to sort a population of cells obtained from Stage IV of the differentiation protocol outlined in Example 1. Two populations of cells were identified: a) $CD56^+CD57^+$, and b) $CD56^+CD57^-$ populations of cells. Populations of $CD56^+CD57^+$ cells were enriched approximately 1.9 fold following sorting. $CD56^+CD57^+$ cells were highly enriched for the expression of markers characteristic of the pancreatic endoderm lineage, including NEUROD, NGN3, PDX1, NKX6.1, NKX2.2, as wells as insulin and glucagon, when compared to unsorted cells or populations of $CD56^+CD57^-$ cells. See FIG. 6, panel a-g. Similar results were observed when populations of cells at Stage V of the differentiation protocol outlined in Example 1 were sorted using antibodies to CD56 and CD57.

Figure 7:
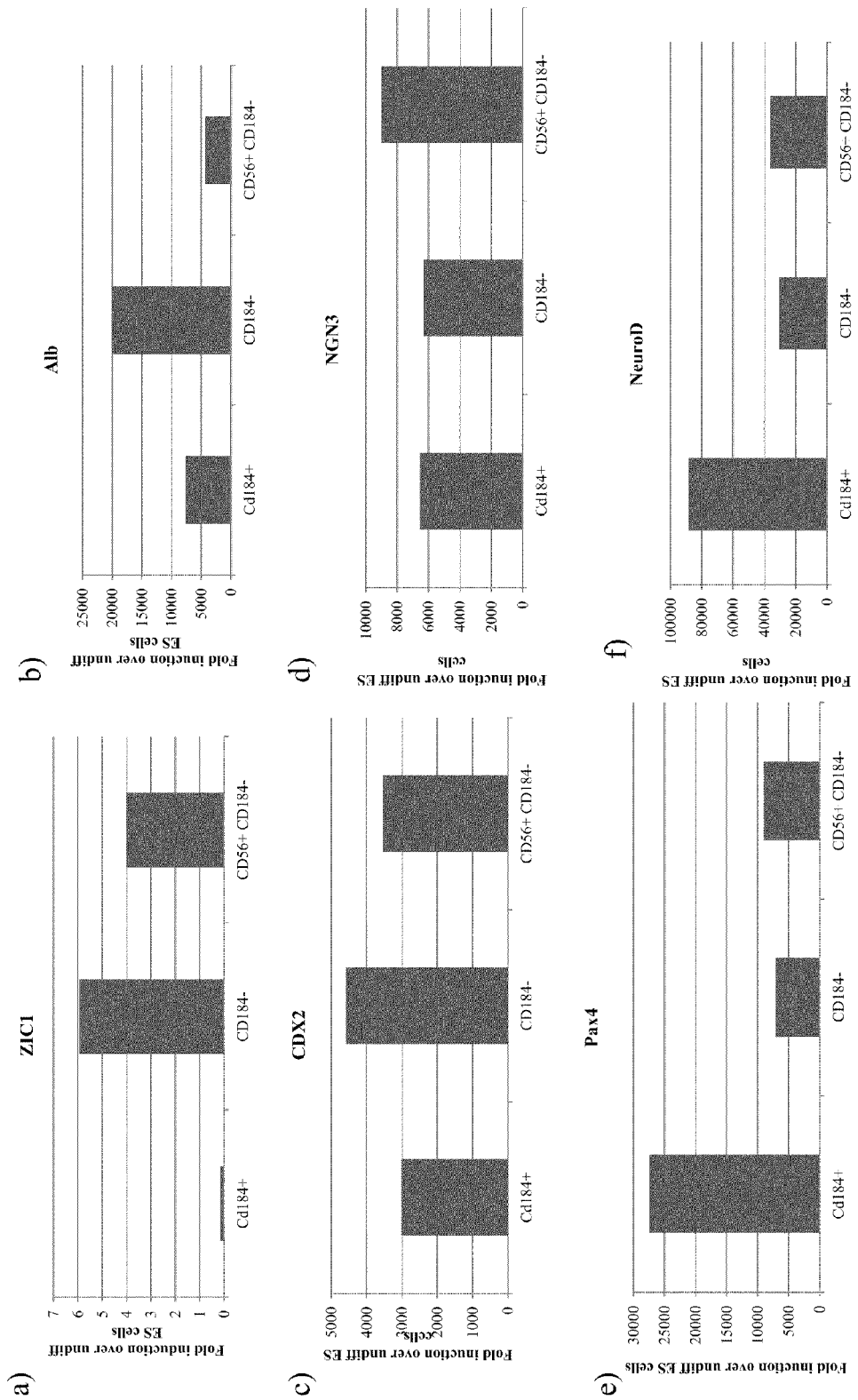
FIG. 7 shows the expression of ZIC1 (panel a), albumin (panel b), CDX2 (panel c), NGN3 (panel d), PAX4 (panel e), NEUROD (panel f), NKX6.1 (panel g), PTF1 alpha (panel h), and PDX1 (panel i), as detected via real-time PCR, in populations of cells sorted using antibodies to CD56 and CD184. Fold expression is shown relative to undifferentiated H1 embryonic stem cells.
Figure 7:
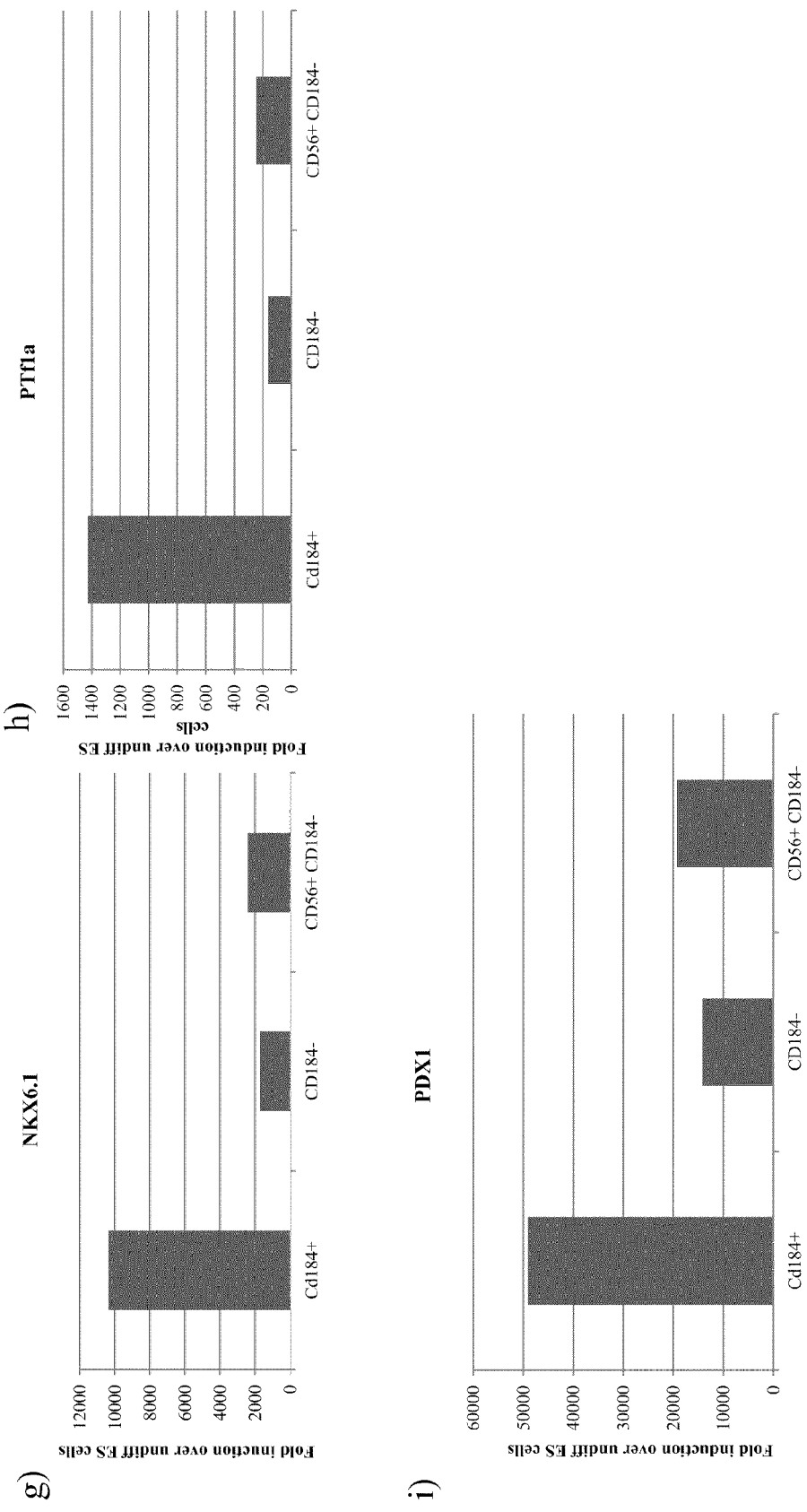

In a sixth series of experiments, antibodies to CD56 and CD184 were used to sort a population of cells obtained from Stage IV of the differentiation protocol outlined in Example 1. Three populations of cells were identified: a) $CD184^+$, b) $CD184^-$, and c) $CD56^+CD184^-$ populations of cells. Table IV summarizes the expression of CD184 in cells before and after the enrichment. Populations of $CD184^+$ cells were enriched for the expression of markers characteristic of the pancreatic endocrine lineage, including PAX4, NEUROD, NKX6.1, PDX1 and PTF1 alpha. The expression of ZIC1, Albumin and CDX2 was decreased. See FIG. 7, panels a-i.

Sorting of Insulin Producing Cells

Figure 8:
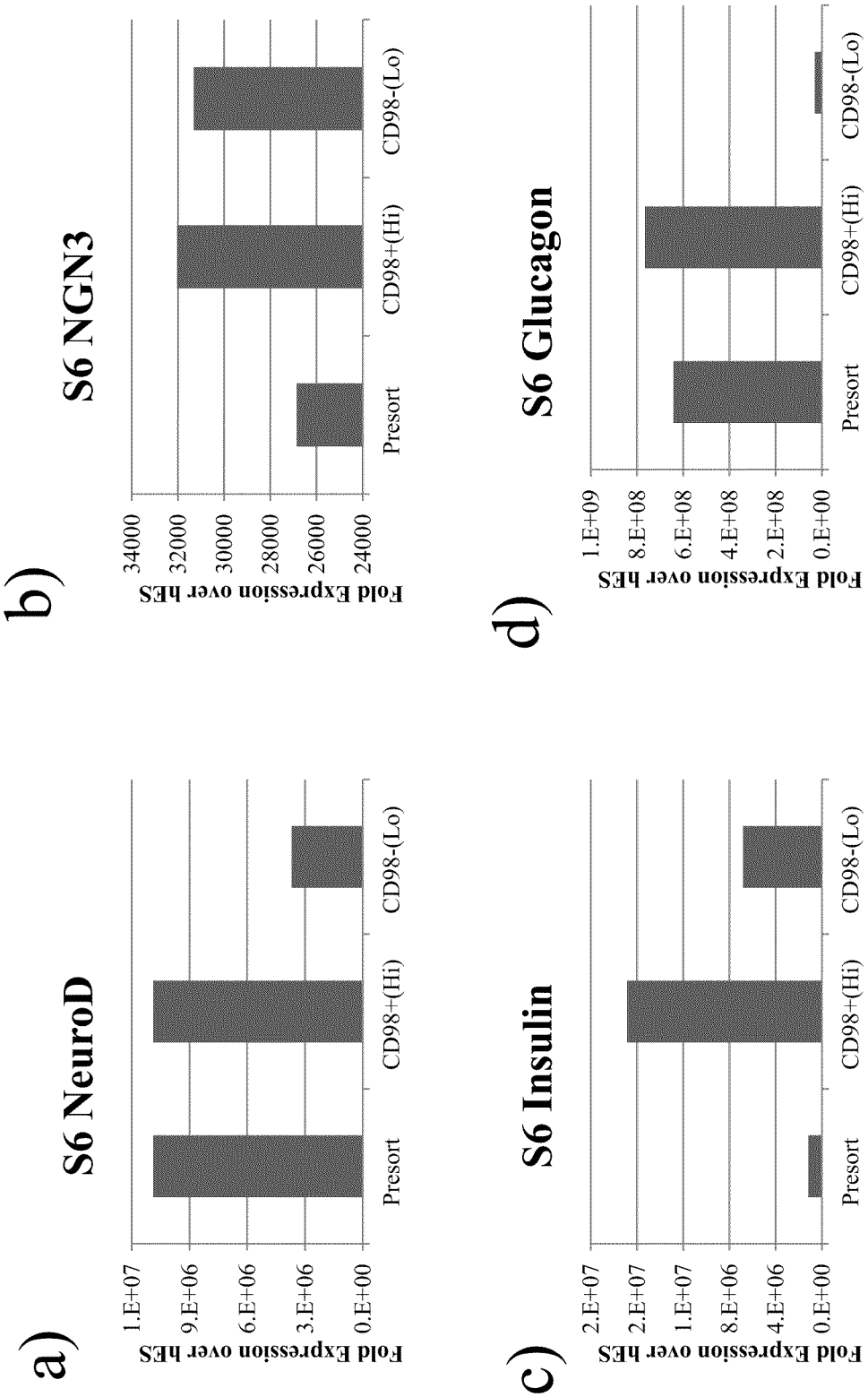
FIG. 8 shows the expression of NEUROD (panel a), NGN3 (panel b), insulin (panel c), and glucagon (panel d), as detected via real-time PCR, in populations of cells sorted using an antibody to CD98. Fold expression is shown relative to undifferentiated H1 embryonic stem cells.

Antibodies to CD98 were used to sort a population of cells obtained from Stage VI of the differentiation protocol outlined in Example 1. Two populations of cells were identified: a) $CD98^{+(Hi)}$, and b) $CD98^{-(Lo)}$ populations of cells. Populations of $CD98^{+(Hi)}$ cells were enriched approximately 1.6 fold following sorting. $CD98^{+(Hi)}$ cells were enriched for the expression of NEUROD, NGN3, insulin, and glucagon. See FIG. 8, panels a-d.

Figure 9:
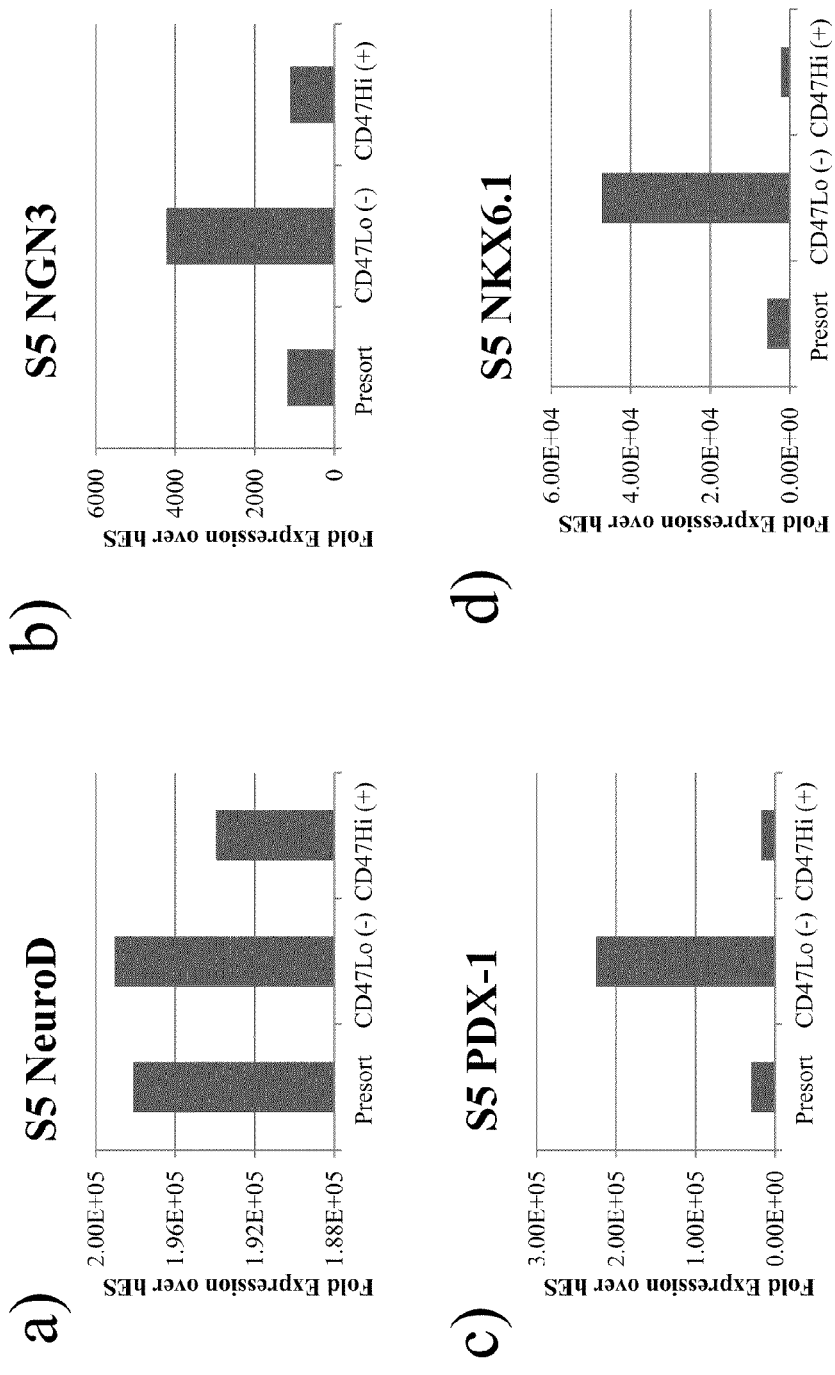
FIG. 9 shows the expression of NEUROD (panel a), NGN3 (panel b), PDX1 (panel c), NKX6.1 (panel d), NKX2.2 (panel e), and PAX4 (panel f), as detected via real-time PCR, in populations of cells sorted using an antibody to CD47. Fold expression is shown relative to undifferentiated H1 embryonic stem cells.
Figure 9:
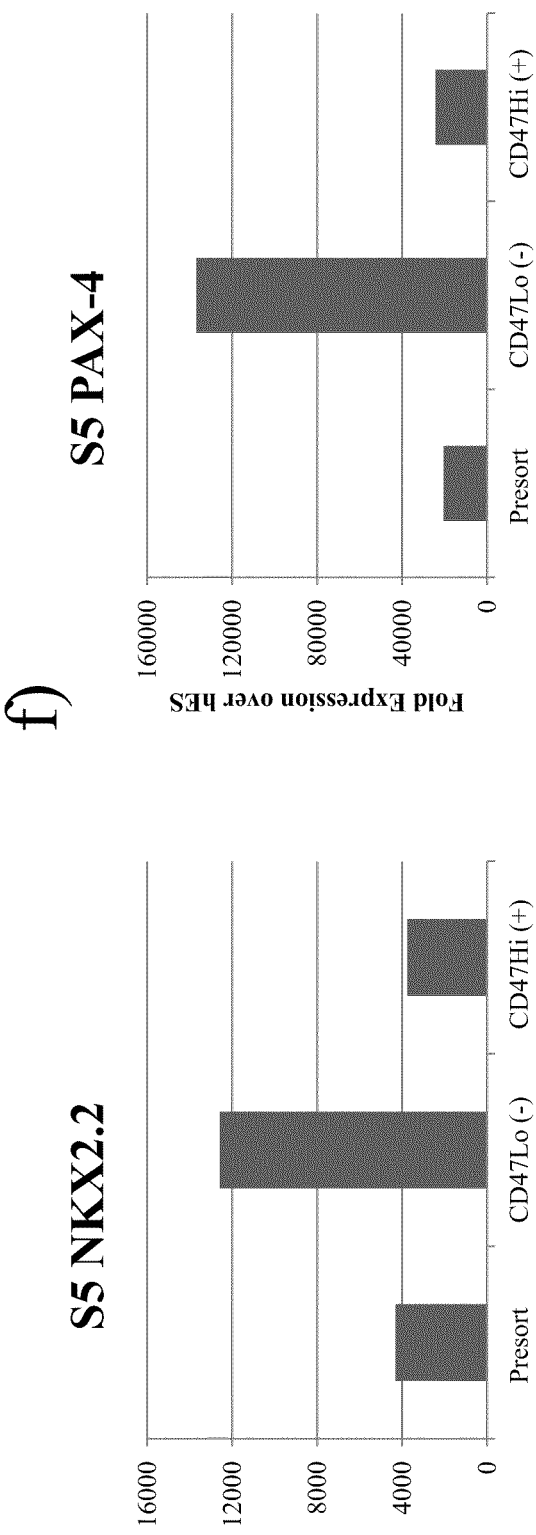

In another series of experiments, antibodies to CD47 were used to sort a population of cells obtained from Stage V of the differentiation protocol outlined in Example 1. Two populations of cells were identified: a) $CD47^{Hi(+)}$, and b) $CD47^{Lo(-)}$ populations of cells. $CD47^{Lo(-)}$ cells were enriched approximately 3.3 fold following sorting. $CD47^{Lo(-)}$ cells were enriched for the expression of NEUROD, NGN3, PDX1, NKX6.1, NKX2.2 and PAX4. See FIG. 9, panels a-f.

Figure 10:
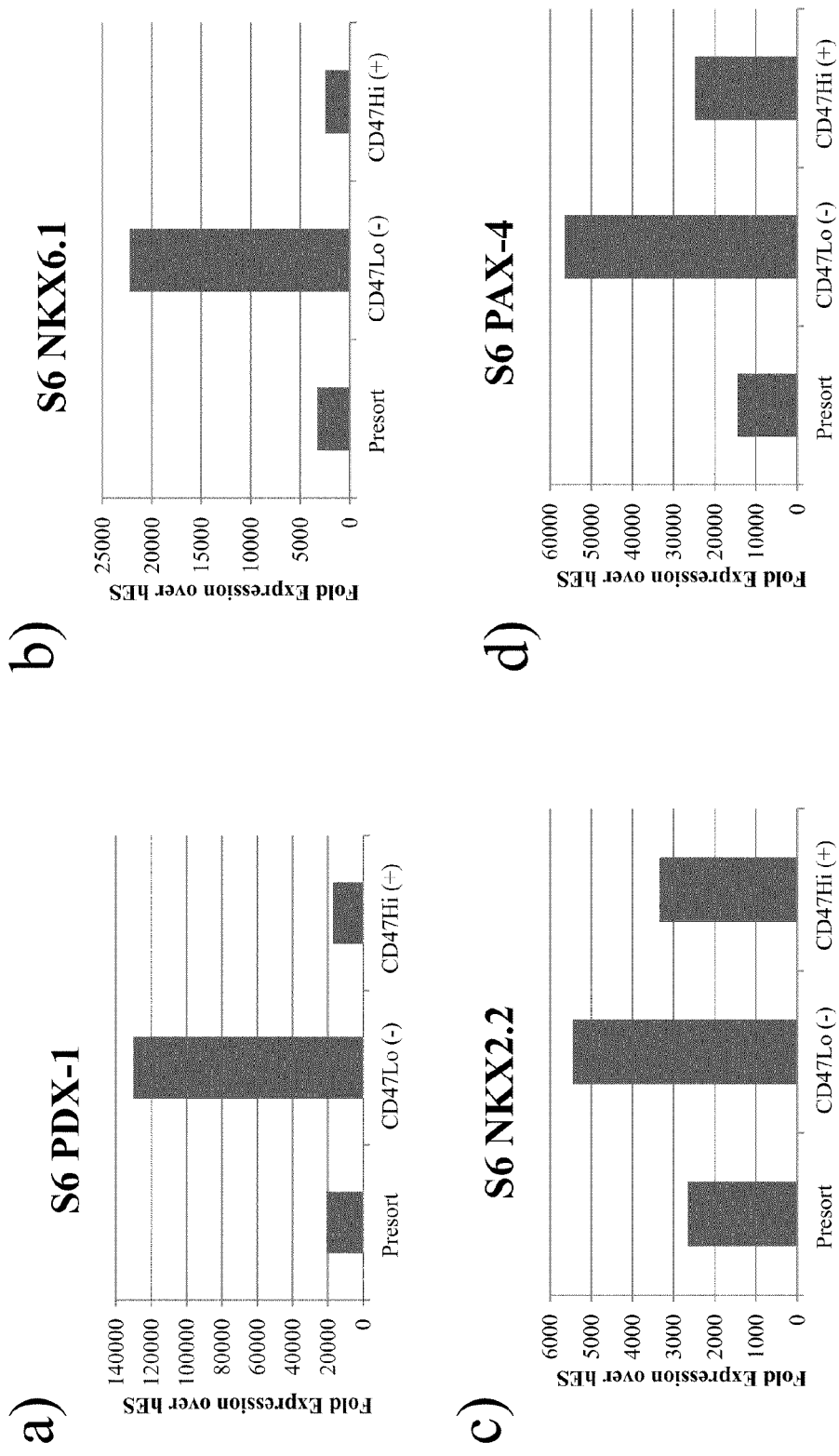
FIG. 10 shows the expression of PDX-1 (panel a), NKX6.1 (panel b), NKX2.2 (panel c), PAX-4 (panel d), PTF1a (panel e), NGN3 (panel f), Insulin (panel g) and glucagon (panel h) as detected via real-time PCR, in populations of cells sorted using an antibody to CD47. Fold expression is shown relative to undifferentiated H1 embryonic stem cells.
Figure 10:
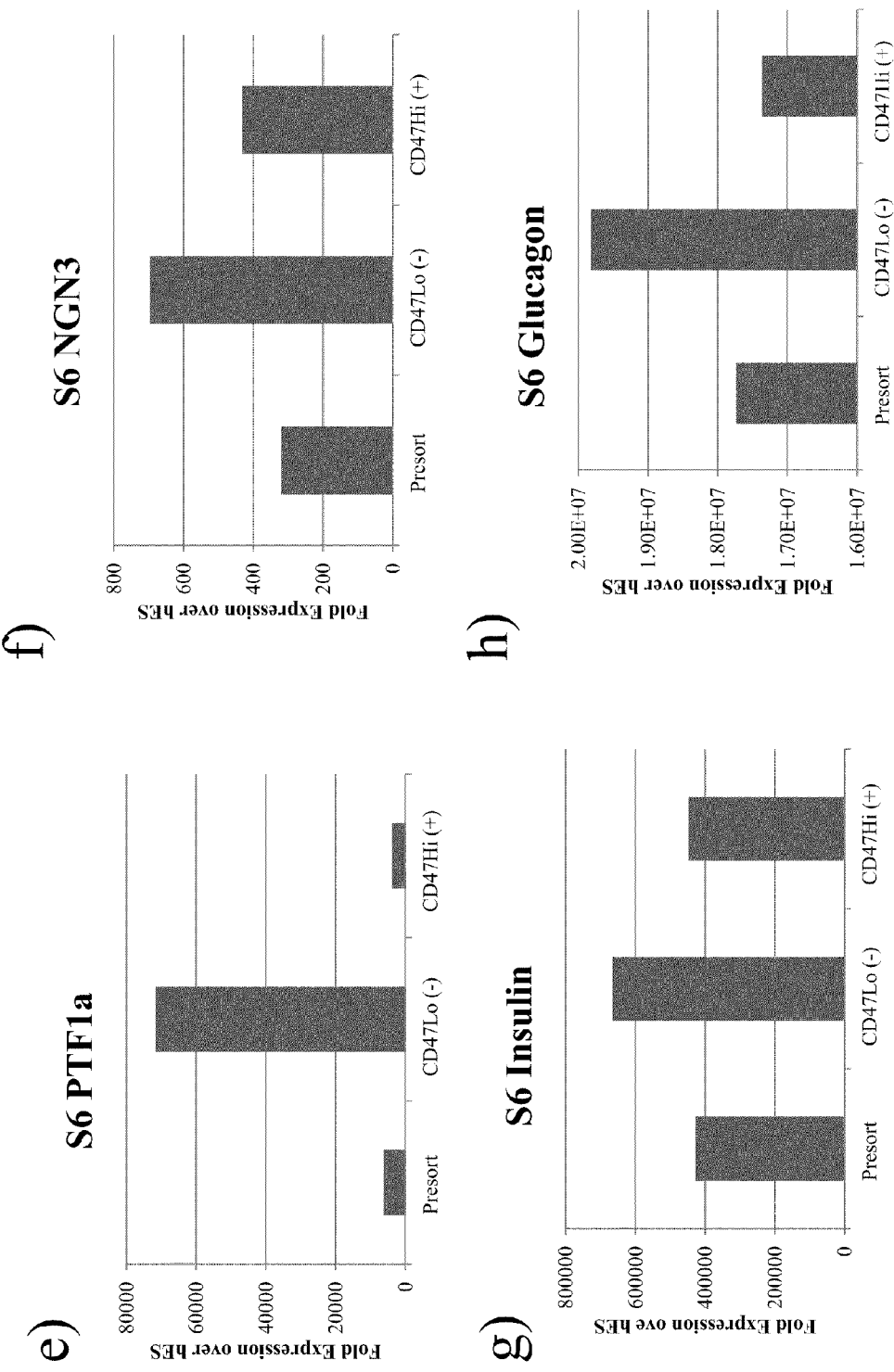

In another series of experiments, antibodies to CD47 were used to sort a population of cells obtained from Stage VI of the differentiation protocol outlined in Example 1. Two populations of cells were identified: a) $CD47^{Hi(+)}$, and b) $CD47^{Lo(-)}$ populations of cells. $CD47^{Lo(-)}$ cells were enriched for the expression of PDX-1, NKX6.1, NKX2.2, PAX-4, PTF1a, NGN3, Insulin and Glucagon. See FIG. 10, panels a-h.

Example 3

Sorting of Lif Receptor Positive Cells at Primitive Gut Tube Stage (Stage 2)

Cells of the human embryonic stem cell line H1 at passage 44 were cultured on MATRIGEL-coated plates, and differentiated into insulin producing cells using the following protocol:
  a. RPMI medium supplemented with 2% fatty acid-free BSA (Catalog #68700, Proliant, IA), and 100 ng/ml activin A (R&D Systems, MN) plus 20 ng/ml WNT-3a (Catalog #1324-WN-002, R&D Systems, MN) plus 8 ng/ml of bFGF (Catalog #100-18B, PeproTech, NJ), for one day followed by treatment with RPMI media supplemented with 2% BSA and 100 ng/ml activin A plus 8 ng/ml of bFGF for an additional two days (Stage 1), then
  b. RPMI+2% BSA+50 ng/ml FGF7+0.25 µM SANT-1 (#S4572, Sigma, MO), for three days (Stage 2), then
  c. DMEM/High-Glucose+1:200 dilution of ITS-X (Invitrogen, CA)+0.1% BSA (Invitrogen, Ca) 50 ng/ml FGF7 (Peprotech, NJ)+0.25 µM SANT-1+2 µM Retinoic acid (RA) (Sigma, MO)+100 ng/ml of Noggin (R & D Systems, MN) and 20 ng/ml of activin A for four days (Stage 3), then
  d. DMEM/High-Glucose+1:200 dilution of ITS-X (Invitrogen, CA)+0.1% BSA (Invitrogen, Ca)+100 ng/ml Noggin+1 µM ALK5 inhibitor (SCIO120)+for three days (Stage 4)

Stage 2 cells were dispersed into single cells using TrypLE Express (Invitrogen, Carlsbad, CA) and washed in stage 4 basal media (DM-Hg+ITS-X+BSA). Released cells were spun and the resulting cell pellet suspended in a staining buffer consisting of 2% BSA, 0.05% sodium azide in PBS (Sigma, MO). As appropriate, the cells were Fc-receptor blocked for 15 minutes using a 0.1% γ-globulin (Sigma) solution. Aliquots (approximately $10^5$ cells) were incubated with Lif receptor-Phycoerythrin (PE) (R & D Systems, MN) conjugated monoclonal antibodies (5 µl antibody per $10^6$ cells). Controls included appropriate isotype matched antibodies and unstained cells. All incubations with antibodies were performed for 30 mins at 4° C. after which the cells were washed with the staining buffer. Stained cells were sorted on a FACS Aria (BD, Ca). RNA (Rneasy Mini Kit, Qiagen, CA) was collected from presort sample, Lif receptor+ fraction and Lif receptor negative fraction. The Lif receptor expression level and pattern is summarized in Table III.

Figure 11:
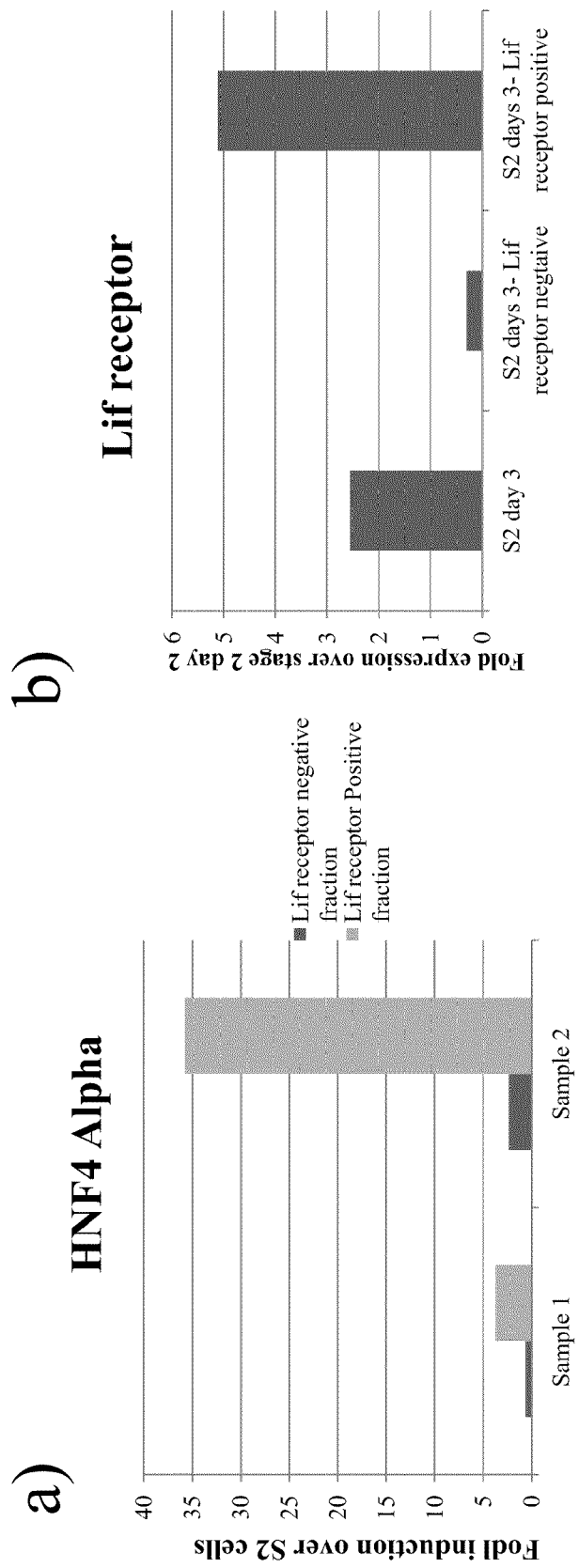
FIG. 11 shows the expression of HNF4 alpha (panel a), and LIF receptor (panel b), as detected via real-time PCR, in populations of cells sorted using an antibody to the LIF receptor. Fold expression is shown relative to unsorted cells at DAY 2 of Stage II of the differentiation protocol outlined in Example 1.

Table III summarizes the expression of Lif receptor at days 2 and 3 of stage 2. By day 3 of stage 2, approximately 70% of the cells expressed Lif receptor. As summarized in Table III, high expression of Lif receptor was unique to stage 2 cells, as stage 3 and 4 cells showed minimal expression of Lif receptor. As shown in FIG. 11, panels a-b, stage 2 cells enriched for the Lif receptor showed a significant increase in expression of HNF4 alpha as compared to unsorted cells or Lif receptor negative cells. Expression of Lif receptor mRNA as measured by real-time PCR was also enhanced in cell fraction containing Lif-receptor positive cells.

Example 4

Magnetic Bead Sorting for Cells for the Depletion of SSEA-4+ Cells to Reduce Tumor Formation in Vivo Expression of the SSEA4 antigen is a key indicator of pluripotency in human embryonic stem cells, and expression of this marker is greatly down regulated during the differentiation process. However, residual SSEA-4 positive cells may be responsible for tumors and/or teratomas that are observed following transplantation of partially differentiated cells. To reduce teratoma formation, methods were developed to deplete contaminating SSEA4$^+$ cells from differentiated cells prior to transplantation.

Cells of the human embryonic stem cell line H1 (passage 40-52) were differentiated to various stages of the differentiation protocol outlined in Example 1. In order to test proof of concept and efficacy of SSEA-4 depletion, this study was first done with cells differentiated only to the primitive gut tube stage (Stage 2 in the differentiation protocol outlined in Example 1) in order to ensure cells still retained higher levels of SSEA-4 expression. In subsequent experiments, cells expressing SSEA-4 were depleted in populations of cells differentiated at Stage 4 of the differentiation protocol outline in Example 1. See Table V for the results observed. Cells were gently released into single cells by incubation in TrypLE Express (Invitrogen #12604, CA) for 2-3 minutes at 37° C. To enhance cell survival and viability during depletion, anti-apoptotic agents including 10 µM Y-27632 (Cat #Y 0503, Sigma, St Louis Mo.) or 0.5 µM Thiazovivin (Cat #04-0017, Stemgent, San Diego, Calif.) were added to the cells prior to collection and in all isolation buffers.

Cells were washed in Isolation Buffer containing $Ca^{2+}$ and $Mg^{2+}$ free phosphate buffered saline (PBS) supplemented with 0.1% BSA and 2 mM EDTA. Between 10-100× $10^6$ cells were re-suspended in isolation buffer a final cell density of $5×10^6$ cells per 500 µl. Twenty five µl SSEA-4 antibody was added per 500 µl of cells and cells incubated for 15-20 minutes at room temperature on a gentle rocker to ensure continuous mixing. Cells were washed in isolation buffer by spinning at 300×g for 8 min. Supernatant was removed and cells re-suspended in original buffer volume and 50 µl of prewashed SSEA-4 Depletion beads (Dyna-Beads® SSEA-4, Invitrogen, #11160D) added for every 500 µl of cell suspension. Cells and beads were mixed and incubated for 15-20 minutes at room temperature with continuous gentle tilting and rotation. Cells were mixed by gentle pipetting and placed on a magnet for 5 min. The supernatant containing SSEA-4 negative cells was transferred to a new tube and the process repeated 2-3 times to remove residual beads. Bead-bound SSEA4$^+$ cells were released from magnetic field and both cells populations counted and processed for FACS and PCR analysis. The expression levels of SSEA4 in undifferentiated H1 cells, primitive gut cells and Stage IV cells, in both pre-sorted and sorted cell fractions is summarized in Table V.

In populations of cells isolated at stage II of the differentiation protocol outlined in Example 1, 20.5% of the cells expressed SSEA4 markers in prior to sorting. In contrast, only 1.8% of the cells expressed the SSEA4 post sort (Table V). The depletion resulted in removal of 91.2% of the SSEA-4 positive cells. In another experiment using endocrine precursor cells, 25.3% of cells expressed SSEA-4 prior to depletion, but only 0.9% expressed SSEA-4 after depletion, resulting in 95.5% removal of SSEA-4 positive cells (Table V). In contrast to differentiated cells, 91.2% of the population of undifferentiated embryonic stem cells expressed SSEA4.

Figure 12:
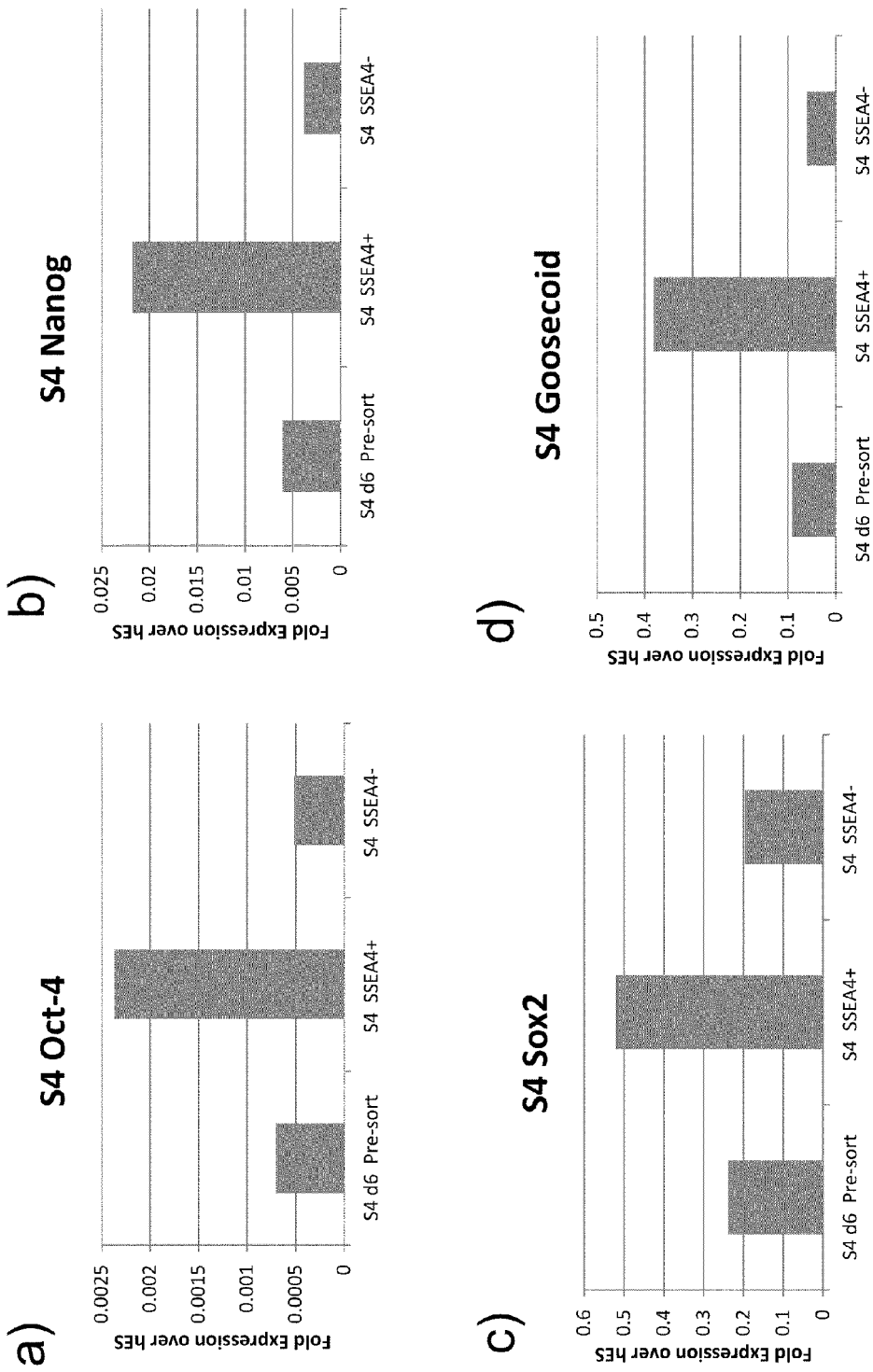
FIG. 12 shows the expression of OCT4 (panel a), NANOG (panel b), SOX2 (panel c), and goosecoid (panel d), as detected via real-time PCR, in populations of cells depleted of cells expressing SSEA4 using magnetic beads. Fold expression is shown relative to undifferentiated H1 embryonic stem cells.

The sorted SSEA4+ cells were highly enriched for the expression of pluripotency markers, including OCT4, NANOG, SOX2 and goosecoid (FIG. 12 panels a-d).

Example 5

Sorting of SSEA4$^{+(HI)}$ and SSEA4$^{-(LO)}$ Cells by FACS

Figure 13:
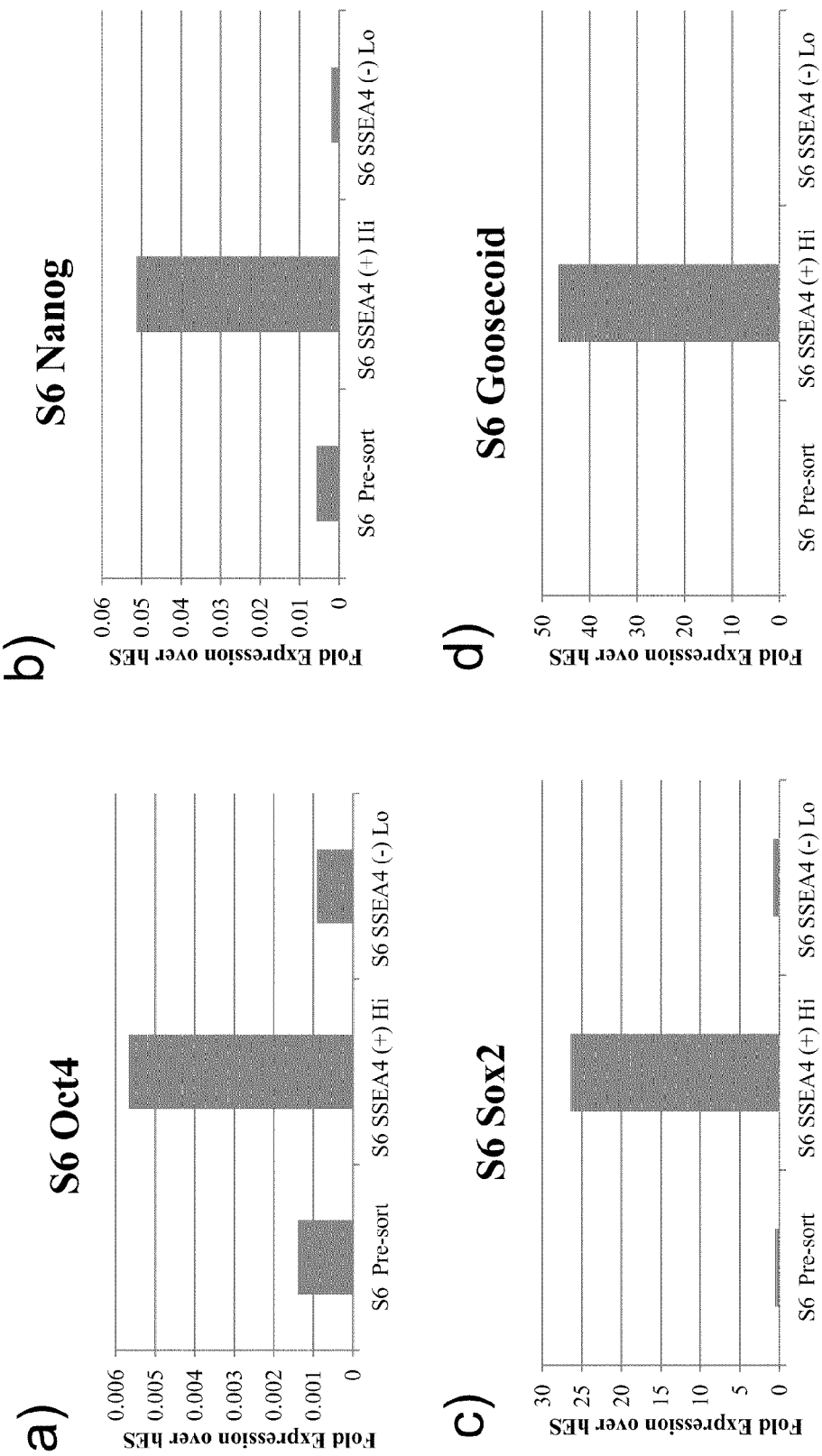
FIG. 13 shows the expression of OCT4 (panel a), NANOG (panel b), SOX2 (panel c), and goosecoid (panel d), as detected via real-time PCR, in populations of cells depleted of cells expressing SSEA4 using FACS. Fold expression is shown relative to undifferentiated H1 embryonic stem cells.

In order to investigate and confirm the depletion of pluripotent-marker (SSEA-4+) enriched cells from differentiated cells by flow cytometry, cells were differentiated to Stage VI as described in Example 1. Cells were released from culture using TrypleE Express cell dissociation buffer and cells prepared for sorting as described in Example 2. The SSEA-4 antibody (R&D Systems, Minneapolis, Minn., Cat #FAB1435P) was used to isolate two cell fractions identified as SSEA-4(+)Hi and SSEA-4(−)Lo cells. Isolated cell fractions were analyzed for expression of pluripotency markers by RT-PCR as described in Example 4. Similar to SSEA-4 depleted and enriched fractions obtained using magnetic beads separation, as described in Example 5, the sorted SSEA-4(+)Hi cells were highly enriched for the expression of pluripotency markers OCT4, NANOG, SOX2 and goosecoid, unlike the SSEA-4(−)Lo cells. See FIG. 13 panels a-d.

Example 6

Transplantation of SSEA-4 Depleted Populations of Cells in Vivo

In pilot experiments, SSEA-4 depleted cells were differentiated to Stage IV of the differentiation protocol outlined in Example 1, and then transplanted into the kidney capsule of mice to test cell survival and engraftment. The data from the transplanted mice is summarized in Table VI.

Five to six-week-old male scid-beige mice (C.B-Igh-1b/ GbmsTac-Prkdc$^{scid}$-Lyst$^{bg}$N7) were purchased from Taconic Farms. Mice were housed in microisolator cages with free access to sterilized food and water. In preparation for surgery, mice were identified by ear tagging and their body weight measured and their blood glucose determine by a hand held glucometer (One Touch, LifeScan). Mice were anesthetized with a mixture of isoflurane and oxygen and the surgical site was shaved with small animal clippers. Mice were dosed with 0.1 mg/kg Buprenex subcutaneously pre-operatively. The surgical site was prepared with successive washes of 70% isopropyl alcohol, 10% povidone-iodide, and 70% isopropyl alcohol and a left lateral incision was made through the skin and muscle layers. The left kidney was externalized and kept moist with 0.9% sodium chloride. A 24G×¾" I.V. catheter was used to penetrate the kidney capsule and the needle was removed. The catheter was then advanced under the kidney capsule to the distal pole of the kidney.

During the preoperative preparation of the mice, the cells were centrifuged in a 1.5 mL microfuge tube and most of the supernatant removed, leaving just enough to collect the pellet of cells. The cells were collected into a Rainin Pos-D positive displacement pipette and the pipette was inverted to allow for the cells to settle by gravity. The excess media was dispensed leaving a packed cell preparation for transplant.

For transplantation, the Pos-D pipette tip was placed firmly in the hub of the catheter and the cells dispensed from the pipette through the catheter under the kidney capsule and delivered to the distal pole of the kidney. The lumen of the catheter was flushed with a small volume of culture media to deliver the remaining cells and the catheter withdrawn. The kidney capsule was sealed with a low temperature cautery and the kidney was returned its original anatomical position. The muscle was closed with continuous sutures using 5-0 vicryl and the skin closed with wound clips. Mice were dosed with 1.0 mg/kg Metacam subcutaneously post-operatively. The mouse was removed from the anesthesia and allowed to fully recover.

Following transplantation, mice were weighed once per week and blood glucose measured twice a week. At various intervals following transplantation, mice were dosed with 3 g/kg glucose IP and blood drawn via the retro-orbital sinus 60 minutes following glucose injection into microfuge tubes containing a small amount of heparin. The blood was centrifuged and the plasma placed into a second microfuge tube and frozen on dry ice and then stored at −80° C. until human c-peptide assay was performed. Human c-peptide levels were determined using the Mercodia/ALPCO Diagnotics Ultrasensitive C-peptide ELISA according to the manufacturer's instructions.

At the time of sacrifice, blood was collected as described above and mice euthanized. The grafts were harvested from the kidney capsule and analyzed by real-time qPCR, immunohistochemistry, and pathology.

Three groups of mice were transplanted with about 3.3 million cells each comprising of i) cell clusters ii) single cells (undepleted) and iii) SSEA4 depleted single cells. Cells differentiated to Stage IV were either released with gentle scarping to make small cell clusters, or released with TrypleE into single cells for SSEA-4 depletion. Following SSEA-4 depletion as outlined in Example 5, both cell clusters and single cell preparations were replated in low attachment plates (Costar, Corning Incorporated, NY Cat #3471) overnight in precursor (Stage IV) cell differentiation medium prior to transplantation. The rock inhibitor Y-27632 dihydrochrolide monohydrate (Sigma, Cat #Y0503) was added to the culture overnight at a concentration of 10 µM. Following transplants, mice were monitored as described above for up to 12 weeks post transplants. Graft survival was not visibly demonstrated in the single cells recipients (depleted or undepleted) but was shown in 2 out of 5 mice receiving cell clusters. One out of 5 mice receiving cell clusters had detectable c-peptide levels at 12 weeks post transplantation. Poor graft survival was attributed to diminished cell quality and low numbers of cells transplanted in the pilot experiment.

The multi-step differentiation of human embryonic cells into mature, pancreatic endocrine cells through several intermediate steps including definitive endoderm (DE), pancreatic endoderm (PE) and pancreatic precursors is associated with dynamic changes in expression of surface markers. Although the differentiation protocol may produce as yet undefined, heterogeneous cell populations of multiple lineages including ectodermal and mesodermal cell types, tracking the changes in expression of surface markers in pancreatic differentiation medium could identify markers potentially useful in cell enrichment and purification. Table VII shows a summary of surface markers that either demonstrated an increase or decrease in expression, that may be useful for negative of positive selection of pancreatic endoderm cells. Markers that decreased in expression during the differentiation process include CD117, CD133, CD181, CD184, CD200, CD221, CD326, CD55, CD57, CD9, and CD98. Markers that increased in expression during the differentiation process include CD13, CD141, CD15, CD318, CD46, CD47, CD49c, CD49e, CD56, and CD73. These markers could singly or in various combinations be used to purify cell populations enriched for pancreatic endoderm and precursors.

Example 7

Flow Cytometric Sorting Procedures

Cells at different stages of maturation were gently released by incubation in TrypLE Express (Invitrogen #12604, CA) for 2-3 minutes at 37° C. and washed twice in BD FACS staining buffer containing 2% BSA (BD #554657, CA). Based on cell yields, 20-50× $10^6$ single cells were re-suspended in 2-3 ml of blocking buffer (0.5% human gamma-globulin diluted 1:4 in staining buffer (BD, CA) for staining. Fluorophore conjugated primary antibodies were added to the cells at a final dilution of 1:20 and cells and incubated for 30 min at 4° C. Following washes, stained cells were re-suspended in 2-3 ml staining buffer and 50-60 µl of 7AAD added for live/dead cell discrimination prior to analysis and cell sorting. Isotype matched control IgG antibodies were used for negative control staining. For calculating fluorophore compensation values prior to sorting, cell were either left unstained or stained with single fluorphore of Fluoroscein isothiocyanate (FITC), Phycoerythrin (PE) or Allophycocyanin (APC) the nuclear dye 7-Aminoactinomucin D (7-AAD).

Cell sorting was done using the BD FACSAria cell sorter and the BD FACSDiva software. Isotype matched control cells were used to establish negative gates for each cell sorting. For each cell sorting experiment, the photomultiplier (PMT) voltage settings were adjusted using the appropriate fluorophore compensation values to produce a bright population (positive (+) or Hi) and dim population or cell subset (Negative (−) or Lo). Typically, positive cells populations (+ or Hi) were of the order of third decade or higher ($10^4$) while negative population were in the first to second decade ($10^2$-$10^3$). Using established gates, cells were sorted using a 100 µM nozzle and a flow rate of 1.0. Following sorting, a small aliquot of cells were analyzed to assess the purity of the sorted cell subsets. RNA was collected from the presort and sorted cells using the Rneasy Mini Kit, Qiagen, CA) for RT-PCR analysis.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE I

Flow Cytometric Characterization of Surface Marker Expression at Different Stages of Endodermal/Pancreatic Differentiation

| Antibody | Synonyms | Vendor/No. | hES | Definitive Endoderm (Stage 1) | Primitive Gut Tube (Stage 2) | Posterior Foregut (Stage 3) | Endocrine Precursor) (Stage 4) | Endocrine Cells (Stage 5) | Mature Endocrine Cells (Stage 6) |
|---|---|---|---|---|---|---|---|---|---|
| BLT-R | | BD#552836 | ND | +/− | +/− | +/− | +/− | +/− | +/− |
| CD105 | Endoglin | Millipore#CBL418F | +/− | +/− | +/− | +/− | +/− | +/− | +/− |
| CD112 | PRR2 | BD#551057 | +/− | +/− | +/− | +/− | +/− | +/− | +/− |
| CD117 | c-kit | BD#341096 | + | ++ | ++ | + | +/− | +/− | +/− |
| CD118 | LIFR, gp190 | R&D#FAB249P | +/− | +/− | + | +/− | +/− | +/− | +/− |
| CD126 | IL-6R | BD#551850 | +/− | +/− | +/− | +/− | +/− | +/− | +/− |
| CD13 | Aminopeptidase N | BD#555394 | +/− | +/− | +/− | +/− | +/− | +/− | +/− |
| CD130 | IL-6Rβ, gp130 | BD#555757 | +/− | +/− | +/− | +/− | +/− | +/− | +/− |
| CD132 | | BD#555900 | +/− | +/− | +/− | +/− | +/− | +/− | +/− |
| CD133 | AC133, prominin-like 1 | MILTENYI#130-090-854 | + | + | ++ | + | + | + | + |
| CD134 | OX-40 | BD#554848 | +/− | +/− | +/− | +/− | +/− | +/− | +/− |
| CD135 | Flt3/Flk2 | BD#558996 | +/− | +/− | +/− | +/− | +/− | +/− | +/− |
| CD137 | | BD#550890 | +/− | +/− | +/− | +/− | +/− | +/− | +/− |
| CD137 Ligand | | BD#559446 | +/− | +/− | +/− | +/− | +/− | +/− | +/− |
| CD140a | PDGFRα | BD#556002 | +/− | +/− | +/− | +/− | +/− | +/− | +/− |
| CD140b | PDGFRβ | BD#558821 | +/− | +/− | +/− | +/− | +/− | +/− | +/− |
| CD142 | | BD#550312 | +/− | +/− | +/− | +/− | + | + | + |
| CD146 | MUC18 | BD#550315 | + | + | + | +/− | + | + | ND |
| CD15 | | BD#551376 | +/− | + | + | + | + | + | + |
| CD161 | | BD#340536 | +/− | +/− | +/− | +/− | +/− | +/− | +/− |
| CD164 | | BD#551298 | +/− | +/− | +/− | +/− | +/− | +/− | +/− |
| CD178 | FasL, CD95L | BD#555293 | +/− | +/− | +/− | +/− | +/− | +/− | ND |
| CD180 | | BD#551953 | +/− | +/− | +/− | +/− | +/− | +/− | +/− |
| CD181 | CXCR1, IL-8RA | BD#555939 | +/− | + | +/− | +/− | +/− | +/− | ND |
| CD183 | CXCR3 | BD#550967 | +/− | +/− | +/− | +/− | +/− | +/− | +/− |
| CD184 | CXCR4, fusin | BD#555976 | +/− | ++ | + | +/− | +/− | +/− | + |
| CD185 | CXCR5 | BD#551959 | +/− | +/− | +/− | +/− | +/− | + | ND |
| CD193 | CCR3 | BD#558165 | +/− | + | +/− | +/− | +/− | +/− | +/− |
| CD195 | CCR5 | BD#555992 | +/− | +/− | +/− | +/− | +/− | +/− | ND |
| CD1b | | BD#555969 | +/− | +/− | +/− | +/− | +/− | +/− | +/− |
| CD20 | | BD#555622 | +/− | +/− | +/− | +/− | +/− | +/− | +/− |
| CD200 | OX-2 | BD#552475 | + | ++ | ++ | + | + | ++ | ++ |
| CD205 | | BD#558069 | +/− | +/− | +/− | +/− | +/− | +/− | +/− |
| CD220 | Insulin-R | BS#559955 | +/− | +/− | +/− | +/− | +/− | +/− | ND |
| CD221 | IGF-1 Rα | BD#555999 | + | ++ | ++ | + | +/− | + | +/− |
| CD24 | | BD#555428 | +++ | +++ | +++ | +++ | +++ | +++ | +++ |

TABLE I-continued

Flow Cytometric Characterization of Surface Marker Expression at Different Stages of Endodermal/Pancreatic Differentiation

| Antibody | Synonyms | Vendor/No. | hES | Definitive Endoderm (Stage 1) | Primitive Gut Tube (Stage 2) | Posterior Foregut (Stage 3) | Endocrine Precursor) (Stage 4) | Endocrine Cells (Stage 5) | Mature Endocrine Cells (Stage 6) |
|---|---|---|---|---|---|---|---|---|---|
| CD243 | MDR-1; P-gp | BD#557002 | +/− | +/− | +/− | +/− | +/− | +/− | +/− |
| CD252 | OX-40 Ligand | BD#558164 | +/− | +/− | +/− | +/− | +/− | +/− | +/− |
| CD26 |  | BD#555436 | +/− | +/− | +/− | +/− | +/− | +/− | +/− |
| CD271 | NGFR | BD#557198 | +/− | ND | +/− | +/− | +/− | +/− | ND |
| CD275 |  | BD#552502 | +/− | +/− | +/− | +/− | +/− | +/− | +/− |
| CD28 |  | BD#555728 | +/− | +/− | +/− | +/− | +/− | +/− | +/− |
| CD29 | Integrin β1 | BD#559883 | +++ | +++ | +++ | +++ | +++ | +++ | +++ |
| CD305 | LAIR1 | BD#550811 | +/− | +/− | +/− | +/− | +/− | +/− | ND |
| CD309 | VEGFR2, KDR | BD#560494 | +/− | +/− | +/− | +/− | +/− | +/− | +/− |
| CD318 | CDCDP1 | R&D#FAB26662P | +/− | +/− | +/− | +/− | + | + | + |
| CD326 | Ep-CAM | BD#347197 | +++ | +++ | +++ | ++ | ++ | ++ | ++ |
| CD33 |  | BD#555450 | +/− | +/− | +/− | +/− | +/− | +/− | +/− |
| CD332 | FGFR2, KGFR2 | R&D#FAB684A | +/− | +/− | +/− | +/− | +/− | +/− | +/− |
| CD340 | ErbB-2, HER2/neu | BD#340553 | +/− | +/− | +/− | +/− | +/− | +/− | +/− |
| CD36 |  | BD#550956 | +/− | +/− | +/− | +/− | +/− | +/− | + |
| CD39 |  | BD#555464 | +/− | +/− | +/− | +/− | +/− | +/− | ND |
| CD42b |  | BD#555472 | +/− | +/− | +/− | +/− | +/− | +/− | +/− |
| CD43 |  | BD#555475 | +/− | +/− | +/− | +/− | +/− | +/− | ND |
| CD44 |  | BD#559942 | +/− | +/− | +/− | +/− | +/− | +/− | +/− |
| CD46 |  | BD#555949 | + | +/− | +/− | +/− | + | + | ND |
| CD47 |  | BD#556046 | +/− | +/− | + | +++ | ++ | ++ | ++ |
| CD49b | α2 Integrin, VLA-2 | BD#555669 | + | +/− | + | + | + | + | +/− |
| CD49c | α3 Integrin, VLA-3 | Abcam#ab30489 | + | + | + | + | + | + | + |
| CD49e | α5 Integrin, VLA-5 | BD#555617 | + | +++ | +++ | ++ | + | + | + |
| CD49f | α6 Integrin, VLA-6 | BD#555735 | + | +/− | + | + | + | + | +/− |
| CD55 |  | BD#555696 | + | ++ | + | +/− | + | + | + |
| CD56 | NCAM | BD#555518 | + | + | + | + | +++ | ++ | +++ |
| CD57 |  | BD#555619 | +++ | +++ | +++ | ++ | + | + | + |
| CD58 | LFA-3 | BD#555920 | + | +/− | +/− | +/− | +/− | +/− | +/− |
| CD63 | LIMP. LAMP-3 | BD#557288 | ND | +/− | +/− | +/− | +/− | +/− | +/− |
| CD66 |  | BD#551480 | +/− | +/− | +/− | +/− | +/− | +/− | +/− |
| CD71 |  | BD#551374 | + | + | + | + | +/− | + | + |
| CD73 |  | BD#550257 | +/− | +/− | +/− | + | + | + | ND |
| CD74 |  | BD#555540 | +/− | +/− | +/− | +/− | +/− | +/− | ND |
| CD88 | C5aR | BD#550494 | +/− | + | +/− | +/− | +/− | +/− | +/− |
| CD9 | P24, MRP-1 | BD#555372 | + | + | +/− | +/− | +/− | +/− | +/− |
| CD91 |  | BD#550496 | +/− | +/− | +/− | +/− | +/− | +/− | +/− |
| CD95 | Apo-1, Fas | BD#555674 | +/− | +/− | +/− | +/− | +/− | +/− | ND |
| CD98 |  | BD#556076 | +++ | +++ | +++ | +++ | ++ | ++ | + |
| CD99 | MIC2, E2 |  | +/− | +++ | +++ | +++ | +++ | +++ | ++ |
| CDw210 | IL-10 R | BD#556013 | +/− | + | +/− | +/− | +/− | +/− | +/− |
| DLL1 |  | R&D#FAB1818A | ND | ND | ND | +/− | +/− | +/− | ND |
| EGFR | ErbB-1, HER1 | BD#555997 | +/− | +/− | +/− | +/− | +/− | +/− | +/− |
| fMLP |  | BD#556016 | +/− | +/− | +/− | +/− | +/− | +/− | +/− |
| MICA/B |  | BD#558352 | +/− | + | +/− | +/− | +/− | +/− | ND |
| Notch1 |  | BD#552768 | +/− | + | +/− | +/− | +/− | +/− | ND |
| SSEA-4 |  | R&D#FAB1435P | +++ | +++ | ++ | + | + | + | + |
| TGFBR3 |  | Lifespan#LS-C76502 | +/− | ND | + | +/− | +/− | + | ND |
| TRA1-60 |  | BD#560193 | +++ | +++ | + | + | + | + | + |
| TRA1-81 |  | BD#560161 | +++ | +++ | + | + | + | + | + |
| TWEAK |  | BD#552890 | +/− | +/− | +/− | +/− | +/− | +/− | +/− |

Key: ND = Not Determined; +/− = 0-10%; + = 10-50%; ++ = 50-85%; +++ = 85-100%

TABLE II

Surface Markers used to Enrich for Pancreatic Cell Precursors

| Surface Markers Used (Single/Combinations) | Stage of Cells Sorted | Vendor/No. | Phenotype of Enriched Populations | % Starting Population | % Sorted Population | Fold Enrichment |
|---|---|---|---|---|---|---|
| CD56/CD13 | Endocrine Precursors (S4) | BD#555518/#55593 | CD56$^+$CD13$^-$ | 64.1 | 82.1 | ~1.3 |
| CD133 | Endocrine Precursors (S4) | Miltenyi#130-090-854 | CD133$^-$ | 48.6 | 92.0 | ~1.9 |
| CD49c(α-3 Integrin) | Endocrine Precursors (S4) | Abcam#ab30489 | CD49c$^{Lo(-)}$ | 31.7 | 95.9 | ~3.1 |
| CD56/CD15 | Endocrine Precursors (S4) | BD#555518/#551376 | CD56$^+$CD15$^{Lo(-)}$ | 26-80 | ND | ND |
| CD15 | Endocrine Precursors (S4) | BD#551376 | CD15$^-$ | 89.6 | 97.5 | ~1.1 |
| CD56/CD57 | Endocrine Precursors (S4) | BD#555518/#555619 | CD56$^+$CD57$^+$ | 31.3 | 59.1 | ~1.9 |
| CD98 | Endocrine Cells (S5) Endocrine Cells (S6) | BD#556076 | CD98$^+$ | 61.3 | 98.9 | ~1.6 |
| CD47 | Endocrine Cells (S5, S6) | BD#556046 | CD47$^-$ | 22.8 | 75.1 | ~3.3 |

TABLE III

Expression levels of LIF Receptor

| | Stage of Differentiation | | | |
|---|---|---|---|---|
| | Stage 2, Day 2 | Stage 2, Day 3 | Stage 3, Day 4 | Stage 4, Day 3 |
| Expression Level (%) | 47% | 70% | 5% | 1% |

TABLE IV

Expression Levels of CD184 Before and After Enrichment

| | Pre-sort | | | | Enriched | |
|---|---|---|---|---|---|---|
| | | | | | CD184+ Fraction | CD184− Fraction |
| Description | CD184+CD56− | CD184+CD56+ | CD184−CD56− | CD184−CD56+ | CD184+ | CD184+ |
| Expression (%) | 1% | 8% | 20% | 70% | 79% | 0.6% |

TABLE V

Expression Levels of SSEA-4 Antigen

| Cells | Stage of Differentiation | SSEA-4 Expression (%) Pre-Depletion | Post-Depletion | % Fold Depletion |
|---|---|---|---|---|
| H1 | Undifferentiated | 91.2 | ND | ND |
| H1 | Primitive Gut (Stage II) | 20.5 | 1.8 | 91.2 |
| H1 | Endocrine Precursors (Stage IV) | 20.1 | 0.9 | 95.5 |

TABLE VI

Summary Data of Mice Transplanted with SSEA-4 Depleted Cells

| Group | Cell Type | Total Cell No. | No. of Mice | Grafts at 12 Week | C-Peptide at 12 Weeks |
|---|---|---|---|---|---|
| 1 | Cell Clusters | 3.3 million | 5 | 3/5 mice visible grafts | 1/5 mice detectable c-peptide |
| 2 | Single Cells | 3.3 million | 5 | 0/5 mice with visible grafts | 0/5 mice detectable c-peptide |
| 3 | SSEA-4 Depleted Single Cells | 3.3 million | 2 | 0/2 mice with visible grafts | 0/2 mice detectable c-peptide |

Un-depleted

TABLE VII

Surface Markers Associated with Differentiation of Human Embryonic Stem cells into Pancreatic and Endodermal Lineages.

| Surface Markers Changes During Differentiation DE→PE→Endocrine | Changes Associated with Surface Markers* | Surface Markers Used To Enrich Pancreatic Endoderm/Endocrine | Cell Fractions Enriched |
|---|---|---|---|
| CD117 | Decrease | ND | — |
| CD13 | Increase | Yes | — |
| CD133 | Decrease | Yes | CD133− |
| CD142 | Increase | ND | — |
| CD15 | Increase | Yes | CD15− |
| CD181 | Decrease | ND | — |
| CD184 | Decrease | Yes | CD184+ |

TABLE VII-continued

Surface Markers Associated with Differentiation of Human Embryonic Stem cells into Pancreatic and Endodermal Lineages.

| Surface Markers Changes During Differentiation DE→PE→Endocrine | Changes Associated with Surface Markers* | Surface Markers Used To Enrich Pancreatic Endoderm/Endocrine | Cell Fractions Enriched |
|---|---|---|---|
| CD200 | Decrease | ND | — |
| CD221 | Decrease | ND | — |
| CD318 | Increase | ND | — |
| CD326 | Decrease | ND | — |
| CD46 | Increase | ND | — |
| CD47 | Increase | Yes | CD47− |
| CD49c | Increase | Yes | CD49c− |
| CD49e | Increase | ND | — |
| CD55 | Decrease | ND | — |
| CD56 | Increase | Yes | CD56+ |
| CD57 | Decrease | Yes | CD57+ |
| CD73 | Increase | ND | — |
| CD9 | Decrease | ND | — |
| CD98 | Decrease | Yes | CD98+ |

Changes associated with Surface Markers Denotes if Expression level of the particular Surface Marker Increased or Decreased as cell were differentiated from Definitive Endoderm (DE, Stage I) to Pancreatic Endoderm (PE, Stage III) and finally to Endocrine Cells (Stage V/VI).

What is claimed is:

1. A method to produce a population of pancreatic endocrine precursor cells enriched for NeuroD, NGN3, PDX-1, and NKX6.1 comprising the steps of:
    a) differentiating a population of human pluripotent stem cells into definitive endoderm cells by treating the pluripotent stem cells with a culture medium supplemented with activin A;
    b) differentiating the definitive endoderm cells into a population of pancreatic endocrine precursor cells;
    c) selecting pancreatic endocrine precursor cells; and
    d) enriching the population of pancreatic endocrine precursor cells for NeuroD, NGN3, PDX-1, and NKX6.1 by screening the population of cells for one of the following surface markers or surface marker combinations to thereby produce an enriched population of cells that is negative for CD13 and:
        1) positive for CD56,
        2) positive for CD56 and CD15$^{lo}$, or
        3) positive for both CD56 and CD57.

2. The method of claim 1, wherein the population of pancreatic endocrine precursor cells is screened for cells that are positive for CD56 and negative for CD13.

3. The method of claim 1, wherein the population of pancreatic endocrine precursor cells is screened for cells that are positive for CD56 and CD15$^{lo}$.

4. The method of claim 1, wherein the population of pancreatic endocrine precursor cells is screened for cells that are positive for positive for both CD56 and CD57.

5. A method to produce a population of pancreatic endocrine precursor cells enriched for NeuroD, NGN3, PDX-1, and NKX6.1 comprising the steps of:
    a) differentiating a population of human pluripotent stem cells into definitive endoderm cells by treating the pluripotent stem cells with a culture medium supplemented with activin A;
    b) differentiating the definitive endoderm cells into a population of pancreatic endocrine precursor cells; and
    c) enriching the population of pancreatic endocrine precursor cells for NeuroD, NGN3, PDX-1, and NKX6.1 by screening the population of cells for cells that are positive for CD56 and CD57, and negative for CD13.

6. A method of enriching a population of pancreatic endocrine precursor cells for NeuroD, NGN3, PDX-1, and NKX6.1 by screening the population of cells for one of the following surface markers or surface marker combinations to thereby produce an enriched population of cells that is negative for CD13 and:
    1) positive for CD56,
    2) positive for CD56 and CD15$^{lo}$, or
    3) positive for both CD56 and CD57.

7. The method of claim 6, wherein the population of pancreatic endocrine precursor cells is screened for cells that are positive for CD56 and negative for CD13.

8. The method of claim 6, wherein the population of pancreatic endocrine precursor cells is screened for cells that are positive for CD56 and CD15$^{lo}$.

9. The method of claim 6, wherein the population of pancreatic endocrine precursor cells is screened for cells that are positive for positive for both CD56 and CD57.

10. The method of claim 6, wherein the pancreatic endocrine precursor cells are derived by in vitro differentiation of human pluripotent stem cells.

11. A method of generating pancreatic endocrine cells comprising:
    obtaining a population of pancreatic endocrine precursor cells enriched for NeuroD, NGN3, PDX-1, and NKX6.1 using the method of claim 1; and
    differentiating the pancreatic endocrine precursor cells into pancreatic endocrine cells.

12. A method of generating pancreatic endocrine cells comprising:
    obtaining a population of pancreatic endocrine precursor cells enriched for NeuroD, NGN3, PDX-1, and NKX6.1 using the method of claim 6; and
    differentiating the pancreatic endocrine precursor cells into pancreatic endocrine cells.

* * * * *